United States Patent [19]
Hemmi et al.

[11] Patent Number: 5,601,802
[45] Date of Patent: Feb. 11, 1997

[54] METHODS OF MRI ENHANCEMENT USING COMPOUNDS HAVING IMPROVED FUNCTIONALIZATION

[75] Inventors: Gregory W. Hemmi, Sunnyvale, Calif.; Jonathan L. Sessler, Austin, Tex.; Tarak D. Mody, Sunnyvale, Calif.

[73] Assignees: Pharmacyclics, Inc., Sunnyvale, Calif.; Board of Trustees, Univ. of TX Sys., Austin, Tex.

[21] Appl. No.: 486,886

[22] Filed: Jun. 7, 1995

Related U.S. Application Data

[63] Continuation of Ser. No. 459,333, Jun. 2, 1995.

[51] Int. Cl.$^6$ .................. C07D 225/00; G01N 24/08
[52] U.S. Cl. .................. 424/9.363; 540/472; 540/474; 530/391.3; 424/9.362; 514/185
[58] Field of Search .................. 540/474, 472; 424/9.3, 9.363; 514/158

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,475,104 | 12/1995 | Sessler et al. | 540/472 |

FOREIGN PATENT DOCUMENTS

| | | |
|---|---|---|
| 0111418 | 6/1984 | European Pat. Off. . |
| 0196515 | 10/1986 | European Pat. Off. . |
| 0233701A2 | 8/1987 | European Pat. Off. . |
| 90/01208 | 8/1990 | WIPO . |
| WO90/10633 | 9/1990 | WIPO . |
| 91/19730 | 12/1991 | WIPO . |
| 92/01781 | 2/1992 | WIPO . |
| WO93/14093 | 7/1993 | WIPO . |
| WO94/09003 | 4/1994 | WIPO . |
| WO94/29316 | 12/1994 | WIPO . |

OTHER PUBLICATIONS

Abid et al., "Lanthanide Complexes of Some macrocyclic Schiff Bases Derived from Pyridine–2,6–dicarboxaldehyde and α,ω–Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrol Macrocycle", *Tetrahedron Lett.*, 25:3269–3270, 1984.

Ansell, "X–Ray Crystal Structure of the Pentagonal Bipyramidal Nickel (11) Complex [Ni$^{11}$(L) (H$_2$O)$_2$] (BF$_4$)$_2$ and the Selective Stabilisation of the Nickel (1) Oxidation State by a Quinquedentate Macrocyclic Ligand", *J. Chem. Soc., Chem. Commun.* pp. 546–547, 1982.

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a Meso–Thiaphlorin", *J. Chem. Soc., Chem. Commun.* pp. 807–809, 1970.

Broadhurst et al., "18— and 22–π–Electron Macrocycles Containing Furan, Pyrrole, and Thiophen Rings", *J. Chem. Soc., Chem. Commun.* pp. 1480–1482, 1969.

Broadhurst et al., "New Macrocyclic Aromatic Systems Related to Porphins", *J. Chem. Soc., Chem. Commun.* pp. 23–24, 1969.

Broadhurst et al., "The Synthesis of 22 π–Electron Macrocycles. Sapphyrins and Related Compounds", *J. Chem. Soc. Perkin Trans.*, 1:2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

(List continued on next page.)

*Primary Examiner*—Mukund J. Shah
*Assistant Examiner*—Pavanaram K. Sripada

[57] ABSTRACT

Texaphyrin metal complexes having improved functionalization include the addition of electron-donating groups to positions 2, 7, 12, 15, 18 and/or 21 and/or the addition of electron-withdrawing groups to positions 15 and/or 18 of the macrocycle. Electron-donating groups at positions 2, 7, 12, 15, 18 and/or 21 contribute electrons to the aromatic π system of the macrocycle which stabilizes the metal complex to demetallation and the imine bonds to hydrolysis. These texaphyrin metal complexes having enhanced stability are useful for localization, magnetic resonance imaging, radiosensitization, radiation therapy, fluorescence imaging, photodynamic therapy, RNA hydrolysis, DNA photocleavage, and applications requiring singlet oxygen production for cytotoxicity. Electron-withdrawing groups at positions 15 and/or 18 render the macrocycle more readily reduced, i.e. the redox potential is lower and the macrocycle more readily gains an electron to form a radical. Such texaphyrins having a low redox potential are useful for radiation sensitization applications.

16 Claims, No Drawings

OTHER PUBLICATIONS

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Gossauer, "Syntheses of Some Unusual Polypyrrole Macrocycles", *Bull. Soc. Chim. Belg.*, 92:793–795, (1983).

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 π–Electron Macrcycle: Pentaphyrin", *J. Chem. Soc., Chem. Commun.*, pp. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Tweedle et al., "Principles of Contrast–Enhanced MRI", in Magnetic Resonance Imaging, 2nd ed. Partain, et al, Eds., W. B. Saunders: Philadelphia, vol. I (1988) 793–809.

Vogel et al., "Porphycene—a Novel Porphin Isomer", *Angew. Chem., Int. Ed. Engl.*, 25:257–259, 1986.

Vogel et al., "2,7,12,17–Tetrapropylporphycene—Counterpart of Octaethylporphyrin in the Porphycene Series", *Angew. Chem., Int. Ed. Engl.*, 26:928–931, 1987.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which absorb in the FAR–red Spectral Region", *SPIE, Optical Methods for Tumor Treatment and Early Diagnosis: Mechanism and Technique*, 1426:318–329, 1991.

Sessler et al., "'Texaphyrin': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide (III) Texaphyrins," *Inorganic Chemistry*, 32(14:3175–3187, 1993.

"2–Äthylamino–2–methyl–propanol–(1)," *Beilstein's Handbuch*, 4:785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," Abstracts of Papers, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivaition of Enveloped Viruses Using Sapphyrin, α 22 π–Electron Expanded Porphyrin: Possible Approaches to Prophylactic Blood Purificaition Protocols," *SPIE Photodynamic Therapy: Mechanisms II*. 1203:233–245, 1990.

Maiya et al., "Ground— and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Iumaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine— and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, "Macrocyclic Polyamines as Biological Cation and Anion Complexones—An Application to Calculi Dissolution," 113–141.

Li and Diederich, "Carriers for Liquid Membrane Transport of Nucleotide 5'-Triphosphates," *J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uanium(VI) and Its Derivatives," *J. Am. Chem. Soc.*, 1978, 1695–1705.

Schmidtchen, "A Non-Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of Macrobicyclid Host Molecules," *Angew, Chem. Int. Ed. Engl.*, 1991, 30(4):442–444.

Sessler et al., "Anion Binding: A New Direction in Porphyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi-Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis-Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Nam–Chiang Wang et al., "Pyrrole chemistry. XVII. Alkylation of the pyrrolyl ambident anion," *Can. J. Chem.*, 55:4112–4116, 1977.

T. D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(22):10,368–10,369, 1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng 1992, 1645 (Proc. Opt. Methods Tumor Treat. Dect.: Mech. Tech. Photodyn. Ther...*, 259–263, 1992.

Thaller et al., "Potential Use of Radiolabelled Porphyrins for Tumor Scanning," *Porphyrin Photosensitizaition*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA·Fe(II)," *Proc. Natl. Acad. Sci. USA*, 82:968–972, 1985.

Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer *bis*(Di–Isobutyl Octadecysiloxy)Silicon 2,3–Naphthalocyanine (*Iso*Bosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[$\alpha$]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Sequence–Specific Modification of Nucleic Acids by Oligonucleotide Derivatives," *FEBS Lett.*, 259(2):335–337, 1990.

Morgan and Skalkos, "Second Generation Sensitizers: Where are We and Where Should we Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1):285–299, 1989.

Praseuth et al., "Sequence–Targeted Photosensitized Reactions in Nucleic Acids by Oligo–$\alpha$–Deoxynucleotides and Oligo–$\beta$–Deoxynucleotides Covalently Linked to proflavin," *Biochemistry*, 27:3031–3038, 1988.

Praseuth et al., "Sequence–Specific Binding and Photocrosslinking of $\alpha$ and $\beta$ Oligodeoxynucleotides to the Major Groove of DNA via Triple–Helix Formation," *Proc. Natl. Acad. Sci. USA*, 84:1349–1353, 1988.

Takasugi et al., "Sequence–Specific Photo–Induced Cross–Linking of the Two Strands of Double–Helical DNA By a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl— and Etioporphycene (OEPc and EtioPc)–Tetra— and Pentacoordinated Zinc Complexes of OEPc," *Angew. Chem. Int. Ed. Engl.*, 32(11):1600–1604, 1993.

Wessel et al., "Porphyrins with Aromatic 26$\pi$–Electron Systems," *Agnew. Chem. Int. Ed. Eng.*, 32(8):1148–1151, 1993.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin et al., "Co(III) Complex Promoted Hydrolysis of Phosphate Diesters: Comparison in Reactivity of Rigid *cis*–Diaquotetraazacobalt (III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions,", *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. AM. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am.Chem. Soc.*, 114:1903–1905, 1992.

Ranganathan et al., "Design of a Chemical Nuclease Model with $(Lys)_2Cu$ as the Core Motif," *Journal of the Chemical Society*,4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication mediated by Retroviral Vectors," *Gene Regulation: Biology of Antisense RNA and DNA*, 261–271, 1992.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates, in Transition Metals in Supramolecular Chemistry," L.Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 19994.

International Search Report mailed Feb. 22, 1994.

International Search Report mailed Feb. 3, 1994.

METHODS OF MRI ENHANCEMENT USING COMPOUNDS HAVING IMPROVED FUNCTIONALIZATION

This application is a continuation application of co-pending U.S. application Ser. No. 08/459,333, filed Jun. 2, 1995, the entire text of which is incorporated herein by reference.

FIELD OF THE INVENTION

The present invention relates to the field of expanded porphyrins, in particular, to texaphyrins having improved functionalization.

BACKGROUND OF THE INVENTION

Certain texaphyrin compounds are described in U.S. Pat. Nos. 4,935,498, 5,162,509, 5,252,720, 5,272,142 and 5,256,399, each of which is incorporated by reference herein. "Texaphyrin" refers to a particular "expanded porphyrin" pentadentate macrocyclic ligand. The compound is capable of existing in both its free-base form and of supporting the formation of a 1:1 complex with a variety of metal cations, such as $Cd^{2+}$, $Hg^{2+}$, $In^{3+}$, $Y^{3+}$, $Nd^{3+}$, $Eu^{3+}$, $Sm^{3+}$, $La^{3+}$, $Lu^{3+}$, $Gd^{3+}$, and other cations of the lanthanide series that are too large to be accommodated in a stable fashion within the 20% smaller tetradentate binding core of the well-studied porphyrins.

Large, or "expanded" porphyrin-like systems are of interest for several reasons: They could serve as aromatic analogues of the better studied porphyrins or serve as biomimetic models for these or other naturally occurring pyrrole-containing systems. In addition, large pyrrole-containing systems offer possibilities as novel metal binding macrocycles. For instance, suitably designed systems could act as versatile ligands capable of binding larger metal cations and/or stabilizing higher coordination geometries than those routinely accommodated within the normally tetradentate ca. 2.0 Å radius porphyrin core. The resulting complexes could have important application in the area of heavy metal chelation therapy, serve as contrast agents for magnetic resonance imaging (MRI) applications, act as vehicles for radioimmunological labeling work, or serve as new systems for extending the range and scope of coordination chemistry.

The desirable properties of texaphyrins are:

1) appreciable solubility, particularly in aqueous media;
2) biolocalization in desired target tissue;
3) low intrinsic toxicity;
4) the ability to attach to solid matrices;
5) the ability to be attached to biomolecules;
6) efficient chelation of divalent and trivalent metal cations;
7) absorption of light in the physiologically important region of 690–880 nm;
8) high chemical stability;
9) ability to stabilize diamagnetic complexes that form long-lived triplet states in high yield and that act as efficient photosensitizers for the formation of singlet oxygen;
10) ability to chelate Gd(III) for magnetic resonance imaging;
11) a redox potential lower than that of oxygen for use as a radiosensitizer.

One of the disadvantages of the texaphyrin metal complexes of prior patents is their short half-life. The $Y^{3+}$ and $In^{3+}$ complexes of the basic texaphyrin have half-lives for decomplexation and/or ligand decomposition of about 3 weeks in 1:1 methanol-water mixtures. While such stability is adequate for some in vitro or in vivo applications, a greater degree of stability in aqueous solution is desirable. For example, a desired solution-phase shelf life of 2–3 years would facilitate the formulation of texaphyrin metal complexes as pharmaceutical products. The new molecules of the present invention address the problems of demetallation of the texaphyrin metal complex and the susceptibility of the imine bonds of the macrocycle to hydrolysis.

The solution to these problems is expected to provide a texaphyrin which has a more desirable shelf life.

SUMMARY OF THE INVENTION

The present invention seeks to solve the above problems by providing texaphyrin metal complexes having improved functionalization compared to those previously described. The improved functionalization is two-fold: firstly, addition of electron-donating groups to positions 2, 7, 12, 15, 18 and/or 21 of the macrocycle contributes electrons to the aromatic $\pi$ system of the macrocycle which stabilizes the metal complex to demetallation and stabilizes the imine bonds to hydrolysis; and secondly, the addition of electron-withdrawing groups to positions 15 and/or 18 renders the macrocycle more readily reduced, i.e. the redox potential will be lower and the macrocycle will more readily gain an electron to form a radical. The addition of substituents to the 12 and 21 positions of the macrocycle also offers steric protection for the imine bonds against possible in vivo enzyme hydrolysis. Thus, the macrocycles of the present invention represent molecules where an attempt has been made to optimize their structure and properties in terms of imine bond stabilization and low redox potential, properties that are expected to be important for radiosensitization as well as other applications.

Exemplary electron-donating groups that may be employed in the practice of the invention include, among others, amino, alkylamino, hydroxyl, acylamino, alkoxy, acyloxy, alkyl, aryl, and alkenyl. Electron-withdrawing groups include halide other than iodide, haloalkyl other than iodoalkyl, formyl, acyl, carboxylic acid, ester, acyl chloride, sulfonic acid, and nitro, among others. Other potential electron-donating or withdrawing groups will be apparent to one of skill in the art in light of the present disclosure.

In certain embodiments, the present invention provides a texaphyrin having the structure:

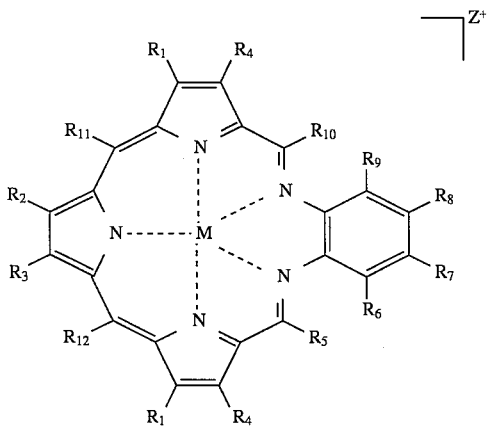

M is H, a divalent metal cation, or a trivalent metal cation.

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, a catalytic group, or a couple to a site-directing molecule or to a catalytic group.

$R_6$ and $R_9$ are independently selected from the groups of $R_1-R_4$, $R_7$ and $R_8$, with the proviso that the halide is other than iodide and the haloalkyl is other than iodoalkyl.

$R_5$ and $R_{10}-R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group.

For this invention, at least one of $R_5$, $R_6$, $R_9$, $R_{10}$, $R_{11}$ and $R_{12}$ is other than hydrogen.

The charge, Z, is an integer value less than or equal to 5. Here, as would be apparent to one skilled in the art, the charge Z would be adjusted so as to account for the choice of metal, M, the pH under consideration, and the substituents $R_1-R_{12}$. For instance, if $R_1$=carboxyl and $R_2-R_{12}$=alkyl and the metal M=$Gd^{+3}$, and the solution is pH=7 (so that $R_1$=$CO_2$—), the charge Z would be zero. The charge would be negative when substituents have a sufficient number of negative charges, for example, when a substituent is an oligonucleotide. The charge would be +5, for example, when the M is $Gd^{+3}$ and the net charge of a substituent(s) is three positive charges.

An aspect of the present invention is an embodiment where a substituent may be an electron-donating group. In this case, $R_1-R_4$ and $R_6-R_9$ are independently hydrogen, hydroxyl, alkyl, aryl, hydroxyalkyl, oxyalkyl, oxyhydroxyalkyl, saccharide, carboxyalkyl, carboxyamidealkyl, a site-directing molecule, a catalytic group, or a couple to a site-directing molecule or to a catalytic group. $R_5$ and $R_{10}-R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group. At least one of $R_5$, $R_6$, $R_9$, $R_{10}$, $R_{11}$ and $R_{12}$ is other than hydrogen and Z is an integer less than or equal to 5.

In another embodiment of the present invention, $R_6$ or $R_9$ may have an electron-withdrawing group. In that case, $R_1-R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, a catalytic group, or a couple to a site-directing molecule or to a catalytic group. $R_5$ and $R_{10}-R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group. $R_6$ and $R_9$ are independently hydrogen, halide other than iodide, formyl, acyl, carboxy, or nitro, where at least one of $R_6$ and $R_9$ is other than hydrogen and Z is an integer less than or equal to 5.

A couple may be an amide, disulfide, thioether, or ether covalent bond. A site-directing molecule may have binding specificity for localization to a treatment site.

It is contemplated that the texaphyrins of the present invention are useful in a variety of applications including use as a photodynamic therapy agent, as a magnetic resonance imaging agent, as a radiation sensitizer, for RNA hydrolysis, and for DNA photocleavage. The use of a texaphyrin diamagnetic-metal complex having a substituent at the 2, 7, 12, 15, 18 and/or 21 position and an absorption range from about 730 to about 770 nanometers includes the following methods which take advantage of the ability of these compounds to produce singlet oxygen: i) a method of deactivating a retrovirus or enveloped virus in an aqueous fluid, the method comprising the steps of adding said texaphyrin metal complex to said aqueous fluid and exposing the mixture to light to effect the formation of singlet oxygen; ii) a method of producing light-induced singlet oxygen comprising subjecting said texaphyrin metal complex to light in the presence of oxygen; iii) a method of photosensitization comprising photoirradiating said texaphyrin; iv) a method of DNA light-induced photocleavage comprising placing said texaphyrin in contact with the RNA or DNA and photoirradiating said texaphyrin; and v) a method of treating a host harboring atheroma or neoplastic tissue comprising administering to the host an effective amount of said texaphyrin complex, the complex exhibiting selective biolocalization in the atheroma or neoplastic tissue relative to surrounding tissues, and photoirradiating the texaphyrin complex in proximity to the atheroma or neoplastic tissue.

Further aspects of the present invention include the use of a texaphyrin paramagnetic-metal complex having a substituent at the 2, 7, 12, 15, 18 and/or 21 position in the following methods which take advantage of the high relaxivity of these compounds: i) a method of enhancement of relaxivity comprising the administration of said texaphyrin; ii) a method of magnetic resonance image enhancement comprising administering to a subject an effective amount of said texaphyrin followed by MR imaging of the subject; iii) a method of detection of atheroma or neoplastic tissue in a subject comprising administering to the subject said texaphyrin in an amount effective to enhance a magnetic resonance image and detecting the atheroma or neoplastic tissue by MR imaging of said subject; iv) a method of imaging an organ in a subject comprising administering to the subject said texaphyrin in an amount effective to enhance a magnetic resonance image of the organ and detecting the organ by MR imaging of said subject; v) a method of imaging an atheroma in a subject comprising administering to the subject said texaphyrin in an amount effective to enhance a magnetic resonance image of the atheroma and detecting the atheroma by MR imaging of said subject; and vi) a method of RNA hydrolysis comprising placing said texaphyrin in contact with the RNA.

A method of treating a host harboring atheroma or neoplastic tissue is also an aspect of the present invention, such method comprising administering to the host as a first agent a texaphyrin detectable-metal complex of the present invention, said complex exhibiting selective biolocalization in the atheroma or neoplastic tissue relative to surrounding tissue; determining localization sites in the host by reference to such texaphyrin-detectable metal complex; administering to the host as a second agent a texaphyrin diamagnetic-metal complex having a substituent at the 2, 7, 12, 15, 18 and/or 21 position and having essentially identical biolocalization property and exhibiting the ability to generate singlet oxygen upon exposure to light; and photoirradiating the second agent in proximity to said atheroma or neoplastic tissue.

The present invention provides a method of radiation therapy for a host harboring atheroma or neoplastic tissue, the method comprising administering to the host a texaphyrin of the present invention, and administering ionizing radiation to the host in proximity to the atheroma or neoplastic tissue. The radiation may be administered either before or after administration of the texaphyrin. The texaphyrin exhibits greater biolocalization in the atheroma or neoplastic tissue relative to surrounding tissues and has radiosensitization properties. An additional step may be included, the step being the determination of localization sites of the atheroma or neoplastic tissue in the host by monitoring texaphyrin concentrations.

One skilled in the art would recognize in light of the present disclosure that sapphyrin-conjugated texaphyrin metal complexes may be used in methods for generating singlet oxygen. Sapphyrin compounds are disclosed in U.S. Pat. Nos. 5,159,065 and 5,120,411 which are incorporated by reference herein.

Texaphyrin metal complexes having increased solution phase stability are expected to be more stable in vivo. Increased stability achieved via specific, designed modifications of the texaphyrin skeleton could give rise to products with modified biolocalization properties. Selective targeting would improve the efficacy and utility of texaphyrins as diagnostic or therapeutic agents for the range of applications discussed herein.

DETAILED DESCRIPTION OF THE PREFERRED EMBODIMENTS

The present invention involves metal complexes of texaphyrins having a substituent(s) at the 2, 7, 12, 15, 18 and/or 21 position(s) of the texaphyrin macrocycle and the synthesis and uses thereof. The nomenclature as used herein defines a substituent $R_{11}$ attached to position 2, $R_{12}$ attached to position 7, $R_5$ attached to position 12, $R_6$ attached to position 15, $R_9$ attached to position 18 and $R_{10}$ attached to position 21 of the macrocycle. The following structure shows a correlation of the IUPAC nomenclature for the positions of the atoms around the periphery of the macrocycle with the positions of the R groups of the present invention.

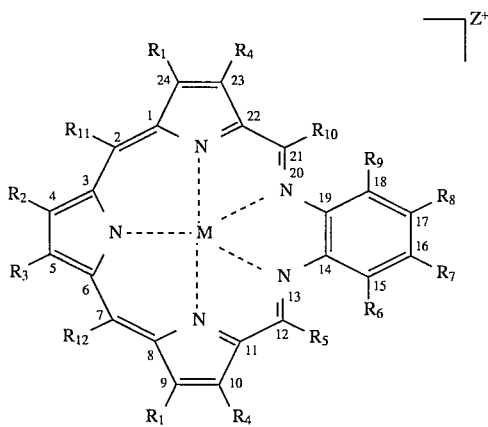

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine.

In a method for synthesizing a texaphyrin metal complex having a substituent at the 2, 7, 12, 15, 18 or 21 position, the method comprises the steps of: i) mixing, in an organic solvent, a nonaromatic texaphyrin having a substituent at the 2, 7, 12, 15, 18 and/or 21 position, a trivalent metal salt, a Brønsted base and an oxidant; and ii) allowing the mixture to react to form an aromatic texaphyrin metal complex having a substituent at the 2, 7, 12, 15, 18, and/or 21 position. A preferred means is to stir at ambient temperature or heat the mixture at reflux for at least two hours.

The corresponding nonaromatic texaphyrin having a substituent at the 2, 7, 12, 15, 18, and/or 21 position is conveniently produced by condensation of a tripyrrane aldehyde or ketone having structure A and a substituted ortho-phenylenediamine having structure B:

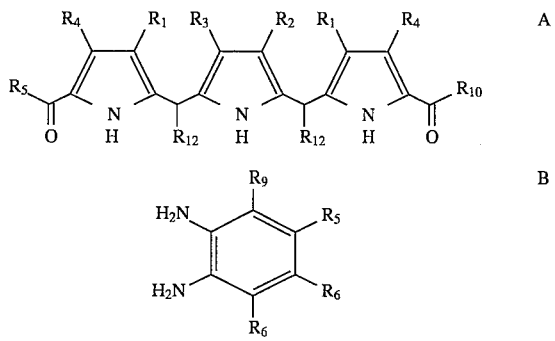

In this embodiment, $R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, or a couple to a site-directing molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$, $R_{10}$, $R_{11}$ and $R_{12}$ are independently hydrogen, alkyl, aryl, hydroxyalkyl, oxyalkyl, oxyhydroxyalkyl, carboxyalkyl, carboxyamidealkyl or a couple to a saccharide or to a site-directing molecule. At least one of $R_5$, $R_6$, $R_9$, $R_{10}$, $R_{11}$ and $R_{12}$ is other than hydrogen.

In a preferred method of synthesis, the Brønsted base is triethylamine or N,N,N',N'-tetramethyl-1,8-diaminonaphthalene ("proton sponge"), and the oxidant is air saturating the organic solvent, oxygen, platinum oxide, o-chloranil or 2,3-dichloro-5,6-dicyano-1,4-benzoquinone. The stirring or heating at reflux step may comprise stirring or heating at reflux the mixture for at least 24 hours. The organic solvent may comprise methanol, or methanol and chloroform, or methanol and benzene, or methanol and dimethylformamide.

In the texaphyrins of the present invention, M is hydrogen, a divalent metal cation, or a trivalent metal cation. The divalent metal cation may be selected from, but is not limited to, the group consisting of Ca(II), Mn(II), Co(II), Ni(II), Zn(II), Cd(II), Hg(II), Fe(II), Sm(II) and UO$_2$(II). The trivalent metal cation may be selected from, but is not limited to, the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

The alkyl, aryl, hydroxyalkyl, oxyalkyl, oxyhydroxyalkyl, saccharide, carboxyalkyl, carboxyamidealkyl, site-directing molecule, or molecule couple is covalently bonded to the texaphyrin via a carbon-carbon, a carbon-nitrogen or a carbon-oxygen bond.

The aryl may be a phenyl group, unsubstituted or substituted with a nitro, carboxy, sulfonic acid, hydroxy, oxyalkyl or halide other than iodide substituent. In this case, the substituent on the phenyl group may be added in a synthetic step after the condensation step which forms the macrocycle.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by two or more functional groups as described herein.

Among the halide substituents, chloride, bromide, fluoride and iodide are contemplated in the practice of this invention with the exception that $R_6$ and $R_9$ are not iodide. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane, straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols having hydroxyl groups; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–3. A preferred oxyalkyl is $O(CH_2CH_2O)_xCH_3$ where $x=1–100$, preferably 1–10, and more preferably, 2–3.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5$)$_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substitutedby one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of $R'$ and $R''$ is a functional group as described herein.

Representative examples of useful amines include a primary, secondary or tertiary amine of an alkyl as described hereinabove.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like.

Saccharide includes oxidized, reduced or substituted saccharide; hexoses such as D-glucose, D-mannose or D-galactose; pentoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol.

Carboxyamidealkyl means alkyl groups containing any number of functional groups, one of which is a secondary or tertiary amide. Carboxyalkyl means alkyl groups containing any number of functional groups, one of which is a carboxyl group.

For the above-described texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to ((2n+1)-2x).

The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than ((2n+1)-q), q is zero or a positive integer less than or equal to 2n+1, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)-2w), R is H, alkyl, hydroxyalkyl, or $C_mH_{((2m+1)-r)}O_zR^b_r$ where m is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)-2w), R is H, alkyl, hydroxyalkyl, or $C_mH_{((2m+1)-r)}O_zR^b_r$ where m is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than ((2n+1)-q), q is zero or a positive integer less than or equal to 2n+1, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)-2w), R is H, alkyl, hydroxyalkyl, or $C_mH_{((2m+1)-r)}O_zR^b_r$ where m is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide.

A couple may be described as a linker, i.e., a reactive group for attaching another molecule at a distance from the texaphyrin macrocycle. An exemplary linker or couple is an amide, disulfide, thioether or ether covalent bond as described in the examples for attachment of oligonucleotides and antibodies.

Certain reactions utilizing the texaphyrin complexes of the present invention, such as hydrolytic cleavage of phosphate ester bonds for example, by may be enhanced by additional catalytic groups appended to the texaphyrin metal complex or to a texaphyrin complex-site directing molecule conjugate. The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine, and the like; amino acids such as L-histidine and L-arginine; derivatives of amino acids such as histamine; polymers of amino acids such as poly-L-lysine, $(LysAla)_n$ or $(LysLeuAla)_n$ where n is from 1–30 or preferably 1–10 or more preferably 2–7, and the like; derivatives thereof; and texaphyrin metal complexes. The term "appended to the texaphyrin-site directing molecule conjugate" means that the catalytic groups are attached either directly to the texaphyrin metal complex or to the texaphyrin complex via a linker or couple of variable length, or are attached to the ligand portion of a texaphyrin complex-ligand conjugate either with or without a linker or couple of variable length.

In one embodiment of the present invention, the texaphyrin is coupled to site-directing molecules to form conjugates for targeted in vivo delivery. "Specificity for targeted sites" means that upon contacting the texaphyrin conjugate with the targeted site, for example under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. Exemplary site-directing molecules contemplated in the present invention include, but are not limited to: oligonucleotides, including oligodeoxyribonucleotides and oligoribonucleotide analogs; polyamides including peptides having affinity for a biological receptor and proteins such as antibodies, low density lipoproteins, the APO protein of lipoprotein; steroids and steroid derivatives; hormones such as estradiol, or histamine; hormone mimics such as morphine; and further macrocycles such as sapphyrins and rubyrins.

Representative examples of useful oligonucleotides include nucleotides, oligonucleotides and polynucleotides primarily composed of adenine, cytosine, guanine, thymine or uracil bases. An oligonucleotide may be derivatized at the base, the sugar, the ends of the chain, or at the phosphate groups of the backbone to promote in vivo stability. Modification of the phosphate groups is preferred in one embodiment of the invention since phosphate linkages are sensitive to nuclease activity. Preferred derivatives are methylphosphonates, phosphotriesters, phosphorothioates, and phosphoramidates, and the like. Additionally, phosphate linkages may be completely substituted with non-phosphate linkages such as amide linkages. Appendages to the ends of the oligonucleotide chain also provide exonuclease resistance. Sugar modifications may include alkyl groups attached to an oxygen of a ribose moiety in a ribonucleotide. In particular, the alkyl group generally has 1 to 4 carbon atoms, and preferably is a methyl group and the methyl group is attached to the 2' oxygen of the ribose. Other alkyl groups may be ethyl or propyl. It is understood that the terms "nucleotide" and "oligonucleotide", as used herein, refer to both naturally-occurring and synthetic nucleotides, poly- and oligonucleotides and to analogs and derivatives thereof.

The term "texaphyrin-oligonucleotide conjugate" means that an oligonucleotide is attached to the texaphyrin in a 5' or a 3' linkage, or to both types of linkages to allow the texaphyrin to be an internal residue in the conjugate. The oligonucleotide or other site-directing molecule may be attached either directly to the texaphyrin via a linker, or a couple of variable length. During treatment, for example, the texaphyrin portion of a texaphyrin metal complex-oligonucleotide conjugate of the present invention is envisioned as being placed in the vicinity of the targeted tissue upon binding of the oligonucleotide to its complementary DNA or RNA.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

The term "a peptide having affinity for a biological receptor" means that upon contacting the peptide with the biological receptor, for example under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

For the above-described texaphyrins, the couple may be an amide, disulfide, thioether or ether covalent bond; the oligonucleotide, the antibody, the hormone or the sapphyrin may have binding specificity for localization to a treatment site; and the biological receptor may be localized to a treatment site.

Generally, water-soluble texaphyrins are preferred for the applications described herein. "Water-soluble" means soluble in aqueous fluids to about 1 mM or better. Such characteristics allow these texaphyrins to be useful in a biological environment. Improved water solubility can be achieved by, for example, substituents chosen from saccharides or hydroxylated substituents.

A preferred embodiment of the present invention is a texaphyrin wherein when either $R_5$ or $R_{10}$ is other than hydrogen, then $R_6$ or $R_9$, respectively, is hydrogen, halide other than iodide (preferably fluoro), or hydroxyl.

Other preferred functionalizations are where $R_6$ and $R_9$ are hydrogen, then $R_5$, $R_{10}$, $R_{11}$ and $R_{12}$ are aryl, lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl. The aryl is preferably phenyl, either unsubstituted or substituted, preferably unsubstituted.

Further preferred embodiments of the present invention are where $R_2$ and $R_3$ are $CH_2CH_3$ and $R_4$ is $CH_3$, where $R_5$ and $R_{10}$ are methyl, or where $R_5$ and $R_{10}$ are $(CH_2)_nCH_3$ where n is 0, 1, 2, 3 or 4. Furthermore, $R_5$ and $R_{10}$ may be aryl having an $R_{13}$ substituent where $R_{13}$ is hydrogen, nitro, carboxy, sulfonic acid, hydroxy, oxyalkyl or halide. A presently preferred aryl is phenyl. The derivatization of the $R_{13}$ group may occur after the condensation of the macrocycle. Preferred substituents for $R_6$ include carboxy, alkyl or carboxyamidealkyl having a tertiary amide linkage. Preferred substituents for $R_7$, $R_8$ and $R_9$ are oxyalkyl or hydroxyalkyl.

Further preferred texaphyrins are wherein each of $R_1$–$R_{12}$ is any one of the substituents of Tables A and B described herein below; more preferred texaphyrins are texaphyrins A1-A56 of Tables A and B described herein below. Preferred metals are Mn(II), Mn(III), Y(III), Lu(III), La(III), In(III), Gd(III), Eu(III), and Dy(III).

Electron-donating substituents at the 2, 7, 12, 15, 18 and/or 21 positions of the macrocycle stabilize the molecule against decomposition processes involving hydrolysis of the imine bonds. Such substituents also stabilize the resulting complex against demetallation by contributing electrons to the aromatic π system. Such electron-donating groups include hydroxyl, alkyl, haloalkyl other than iodoalkyl, aryl, hydroxyalkyl, oxyalkyl, oxyhydroxyalkyl, saccharide, carboxyalkyl, carboxyamidealkyl, a site-directing molecule, or a couple to any of these molecules. Hydrolysis-resistant texaphyrin metal complexes are useful for localization, magnetic resonance imaging, radiosensitization, radiation therapy, fluorescence imaging, photodynamic therapy and applications requiring singlet oxygen production for cytotoxicity.

Electron-withdrawing substituents at the 15, 16, 17 and/or 18 positions of the macrocycle destabilize the aromatic π system and render the macrocycle more readily reduced, i.e. more easily able to gain an electron to form a radical. Such electron-withdrawing groups include halide other than iodide, formyl, acyl, carboxy, or nitro substituents. Readily reducible texaphyrin metal complexes are useful for radiosensitization where the extent of radiation damage is dependent on the generation of hydroxyl and texaphyrin radicals.

The photophysical properties of prior texaphyrin metal complexes are reported in U.S. Pat. No. 5,252,720 and include strong low energy optical absorptions in the 690–880 nm spectral range, a high triplet quantum yield and efficient production of singlet oxygen. Texaphyrin metal complexes of grandparent application Ser. No. 08/135,118, incorporated by reference herein, demonstrate enhanced cytotoxicity from radiation and enhanced nucleic acid strand scission in the presence of a gadolinium(III) metallotexaphyrin complex. U.S. Pat. No. 5,252,720 describes photosensitized inactivation of enveloped viruses and magnetic resonance imaging (MRI) of atheroma, liver, kidney and tumor using various substituted texaphyrin metal complexes. Altering the polarity and electrical charges of side groups of the texaphyrin macrocycles alters the degree, rate, and site(s) of binding to free enveloped viruses such as HIV-1 and to virally-infected peripheral mononuclear cells, thus modulating photosensitizer take-up and photosensitization of leukemia or lymphoma cells contaminating bone-marrow. Powerful techniques include the use of these texaphyrins in magnetic resonance imaging followed by photodynamic therapy in the treatment of atheroma and benign and malignant tumors, or followed by sensitized X-ray treatment.

It is contemplated that the texaphyrins of the present invention will prove useful in a variety of applications. One example is in a method of deactivating a retrovirus or enveloped virus in an aqueous fluid. Such a method comprises the step of adding a texaphyrin metal complex having a substituent at the 2, 7, 12, 15, 18 and/or 21 position to said aqueous fluid and exposing the mixture to light to effect the formation of singlet oxygen. The aqueous fluid may be a biological fluid, blood, plasma, edema tissue fluid, ex vive fluid for injection into body cavities, cell culture media, or a supernatant solution from cell culture and the like.

In blood, an exemplary viral deactivating method would include: i) mixing with blood in vitro or ex vive a texaphyrin metal complex having a substituent at the 2, 7, 12, 15, 18 and/or 21 position capable of producing singlet oxygen when irradiated in the presence of oxygen; and ii) photoirradiating the mixture in vitro or ex vivo to produce singlet oxygen in a quantity cytotoxic to said retrovirus or enveloped virus. Exemplary retroviruses or enveloped viruses include herpes simplex virus I, cytomegalovirus, measles virus, or human immunodeficiency virus HIV-1. However, it is contemplated that the utility of the invention is not limited to these viruses. Preferred metal cations are diamagnetic metal cations and a preferred metal complex is the Lu(III), La(III) or In(III) complex of said texaphyrin.

A further application of the present invention is a method of light-induced singlet oxygen production comprising subjecting a texaphyrin metal complex having a substituent at the 2, 7, 12, 15, 18 and/or 21 position to light in the presence of oxygen. A method of photosensitization comprising the production of singlet oxygen by irradiating a texaphyrin metal complex having a substituent at the 2, 7, 12, 15, 18 and/or 21 position and an absorption range from about 730 to about 770 nanometers to form long-lived triplet states in high yield is another embodiment of the present invention. A texaphyrin metal complex having a substituent at the 2, 7, 12, 15, 18 and/or 21 position has the structure as described previously herein; however, for these applications, M is a diamagnetic metal cation, for example, In(III), Zn(II), Cd(II), Lu(III) or La(III). "Intrinsic biolocalization selectivity" means having an inherently greater affinity for certain tissues relative to surrounding tissues.

Further aspects of the present invention include the use of a texaphyrin paramagnetic-metal complex having a substituent at the 2, 7, 12, 15, 18 and/or 21 position in the following methods which take advantage of the high relaxivity of these compounds: i) a method of enhancement of relaxivity comprising the administration of said texaphyrin; ii) a method of magnetic resonance image enhancement comprising administering to a subject an effective amount of said texaphyrin; iii) a method of detection of neoplastic tissue in a patient comprising the steps of administering to a patient said texaphyrin in an amount effective to enhance a magnetic resonance image and detecting neoplastic tissue by magnetic resonance imaging of said patient; iv) a method of imaging an organ in a patient comprising administering to a patient said texaphyrin in an amount effective to enhance a magnetic resonance image of the organ and detecting the organ by magnetic resonance imaging of said patient (the organ may be liver, kidney or the upper GI tract); v) a method of imaging atheroma in a patient comprising administering to a patient said texaphyrin in an amount effective to enhance a magnetic resonance image of atheroma and detecting atheroma by magnetic resonance imaging of said patient.

For use in these imaging applications, the texaphyrin paramagnetic-metal complex has the structure as described herein; however, M is a paramagnetic metal cation, such as a trivalent lanthanide metal other than La(III), Lu(III) and Pm(III). In particular, M may be Mn(II), Mn(III), Fe(III) or Gd(III) and is preferably Gd(III).

A method of treating a host harboring atheroma or benign or malignant tumor cells is also an aspect of the invention. An exemplary preferred method includes administering to the host as a first agent a texaphyrin detectable-metal complex having a substituent at the 2, 7, 12, 15, 18 and/or 21 position, said complex exhibiting selective biolocalization in such atheroma or tumor cells relative to surrounding tissue; determining localization sites in the host by reference to such detectable metal; administering to the host as a second agent a texaphyrin diamagnetic-metal complex having a substituent at the 2, 7, 12, 15, 18 and/or 21 position and having essentially identical biolocalization property and exhibiting the ability to generate singlet oxygen upon exposure to light; and photoirradiating the second agent in proximity to said atheroma or tumor cells.

In the above-described method, the first agent is further defined as being a texaphyrin paramagnetic-metal complex, the paramagnetic metal serving as the detectable metal. In this case, determination of localization sites occurs by magnetic resonance imaging; and the second agent is a texaphyrin diamagnetic-metal complex. The paramagnetic metal is most preferably Gd(III) and the diamagnetic metal is most preferably La(III), Lu(III) or In(III). A variation of this method uses as a first agent a texaphyrin-gamma emitting metal complex that serves as a detectable metal, determination of localization sites occurs by gamma body scanning and the second agent is a texaphyrin-diamagnetic metal complex. A further variation uses as a first agent a texaphyrin which exhibits fluorescence, e.g., a texaphyrin that is non-metallated (M=H) or is complexed with a diamagnetic metal. Localization means is then by fluorescent spectroscopy. M is hydrogen or a detectable metal, preferably detectable by magnetic resonance imaging, by gamma scanning or fluorescence spectroscopy. "Detectable" as used herein means that the location may be found by localization means such as magnetic resonance imaging if the metal is paramagnetic, gamma ray detection if the metal is gamma emitting or using monochromatic X-ray photon sources or by fluorescence. "Selective biolocalization" means having an inherently greater affinity for certain tissues relative to surrounding tissues. "Essentially identical biolocalization property" means the second agent is a texaphyrin derivative having about the same selective targeting characteristics in tissue as demonstrated by the first agent.

A method of treating a host harboring tumor cells comprises the steps of: i) administering to the host an effective amount of a texaphyrin diamagnetic-metal complex having a substituent at the 2, 7, 12, 15, 18 and/or 21 position, the complex exhibiting selective biolocalization in the tumor cells relative to surrounding tissue; and ii) photoirradiating the texaphyrin-diamagnetic metal complex in proximity to the tumor cells. The photoirradiating is generally at a wavelength of about 730 to 770 nanometers or may be from laser light. In these embodiments, the diamagnetic metal will typically be In(III), La(III) or Lu(III).

The present invention provides a method of radiation therapy for a host harboring a tumor. The method includes the steps of administering to the host a texaphyrin having a substituent in the 2, 7, 12, 15, 18 and/or 21 position(s), and administering ionizing radiation to the host in proximity to the tumor either before or after administration of the texaphyrin, following procedures as described in U.S. Ser. No. 08/135,118, incorporated herein by reference. The texaphyrin exhibits greater biolocalization in the tumor relative to non-tumor tissue and has radiosensitization properties. A tumor may be a benign or malignant tumor or may be atheroma. A texaphyrin having radiosensitization properties enhances cytotoxicity from ionizing radiation as compared to control experiments without the texaphyrin. Ionizing radiation includes but is not limited to x-rays, and internal and external gamma emitting radioisotopes.

The texaphyrin may be complexed with a metal; however, a metal is not necessary for radiosensitization. The metal is important to the stability of the texaphyrin complex. The ionizing radiation may be from an external source or the metal may be a radioactive metal. In the latter case, the ionizing radiation is from the radioactive metal in combination with radiation from an external source.

An improved method of treating a host harboring a tumor comprises the further step of determining localization sites in the host by monitoring texaphyrin concentrations. "Monitoring texaphyrin concentrations" means measuring fluorescence of an administered free base texaphyrin or by reference to the metal of an administered texaphyrin metal complex. If the metal is paramagnetic, then magnetic resonance imaging is used for measurement; if the metal is a gamma emitting radioactive metal, then gamma emission is used for measurement.

A further improved method of treating a host harboring a tumor comprises the additional steps of administering to the host as a second agent a texaphyrin-diamagnetic metal complex having a substituent at the 2, 7, 12, 15, 18 and/or 21 position and having essentially identical biolocalization property and administering ionizing radiation and photoirradiation in proximity to the tumor.

In these methods, determining localization sites may occur by observing fluorescence from the texaphyrin. When the first agent is complexed with a metal, the metal may be a gamma-emitting metal and determining localization sites would occur by gamma body maging, or the metal may be a paramagnetic metal and determining localization sites would occur by magnetic resonance imaging.

"Exhibiting greater biolocalization in the tumor relative to non-tumor tissue" means having an inherently greater affinity for tumor tissue relative to non-tumor tissue. The second agent has essentially identical biolocalization property as the first agent and exhibits the ability to generate singlet oxygen upon exposure to light. The photodynamic effect may be derived from anaerobic electron transfer processes. A preferred diamagnetic metal texaphyrin complex is the Lu(III), La(III) or In(III) complex of a texaphyrin. "Essentially identical biolocalization property" means the second agent is a texaphyrin derivative having about the same selective targeting characteristics in tissue as demonstrated by the first agent. The first agent and the second agent may be the same texaphyrin.

A preferred embodiment of the present invention is a method of radiation therapy for a host harboring a tumor comprising the steps of i) administering to the host a pharmaceutically effective amount of the Gd complex of a texaphyrin having a substituent at the 2, 7, 12, 15, 18 and/or 21 position(s); and ii) administering ionizing radiation to the host in proximity to the tumor, either before or after administration of the texaphyrin metal complex.

Another aspect of this invention is a method of imaging atheroma in a host comprising the administration to the host as an agent a detectable-metal texaphyrin complex having a substituent at the 2, 7, 12, 15, 18 and/or 21 position(s), said complex exhibiting selective biolocalization in such atheroma; and imaging the atheroma in the host by reference to such detectable metal. The agent is preferably a detectable-metal texaphyrin complex having a paramagnetic metal serving as said detectable metal, and imaging of the atheroma occurs by magnetic resonance imaging. The paramagnetic metal is preferably Gd(III).

For the above-described uses, texaphyrins are provided as pharmaceutical preparations. A pharmaceutical preparation of a texaphyrin may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a texaphyrin of the present invention and the pharmaceutically acceptable carriers are then easily administered in a variety of dosage forms such as injectable solutions.

For parenteral administration, solutions of the texaphyrin in sesame or peanut oil, aqueous propylene glycol, or in sterile aqueous solution may be employed. Such aqueous solutions should be suitably buffered if necessary and the liquid diluent first rendered isotonic using, for example, saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The following examples describe the synthesis of texaphyrin metal complexes having a substituent(s) at the 2, 7, 12, 15, 18 and/or 21 position(s) of the macrocycle. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Synthesis of Compounds A3, A5, A6 and A7

This example describes the synthesis of a texaphyrin metal complex having substituents at the 12 ($R_5$), 15 ($R_6$), 18 ($R_9$) and 21 ($R_{10}$) positions of the macrocycle as depicted in Scheme A, parts 1 and 2; a tripyrrane ketone A5, a substituted ortho-phenylenediamine A3, a nonaromatic texaphyrin A6, and a metal complex of aromatic texaphyrin A7.

All solvents and reagents are of reagent grade quality, available commercially, and are used without further purification. Sigma lipophilic Sephadex (LH-20–100) and Merck type 60 (230–400 mesh) silica gel are used for column chromatography.

$^1$H and $^{13}$C NMR spectra are obtained on a General Electric QE-300 (300 MHz.) spectrometer. Electronic spectra are recorded on a Beckman DU-7 spectrophotometer in $CHCl_3$. Infrared spectra are recorded, as KBr pellets, from 4000 to 600 cm$^{-1}$ on a Nicolet 510P FT-IR spectrophotometer. Chemical ionization mass spectrometric analyses (CI MS) are made using a Finnigan MAT 4023. Low resolution and high resolution fast atom bombardment mass spectrometry (FAB MS) are performed with a Finnigan-MAT TSQ-70 and VG ZAB-2E instruments, respectively. A nitrobenzyl alcohol (NBA) matrix is utilized with CHCl$_3$ as the co-solvent. Elemental analyses are performed by Atlantic Microlab, Inc. Melting points are measured on a Mel-temp apparatus and are uncorrected.

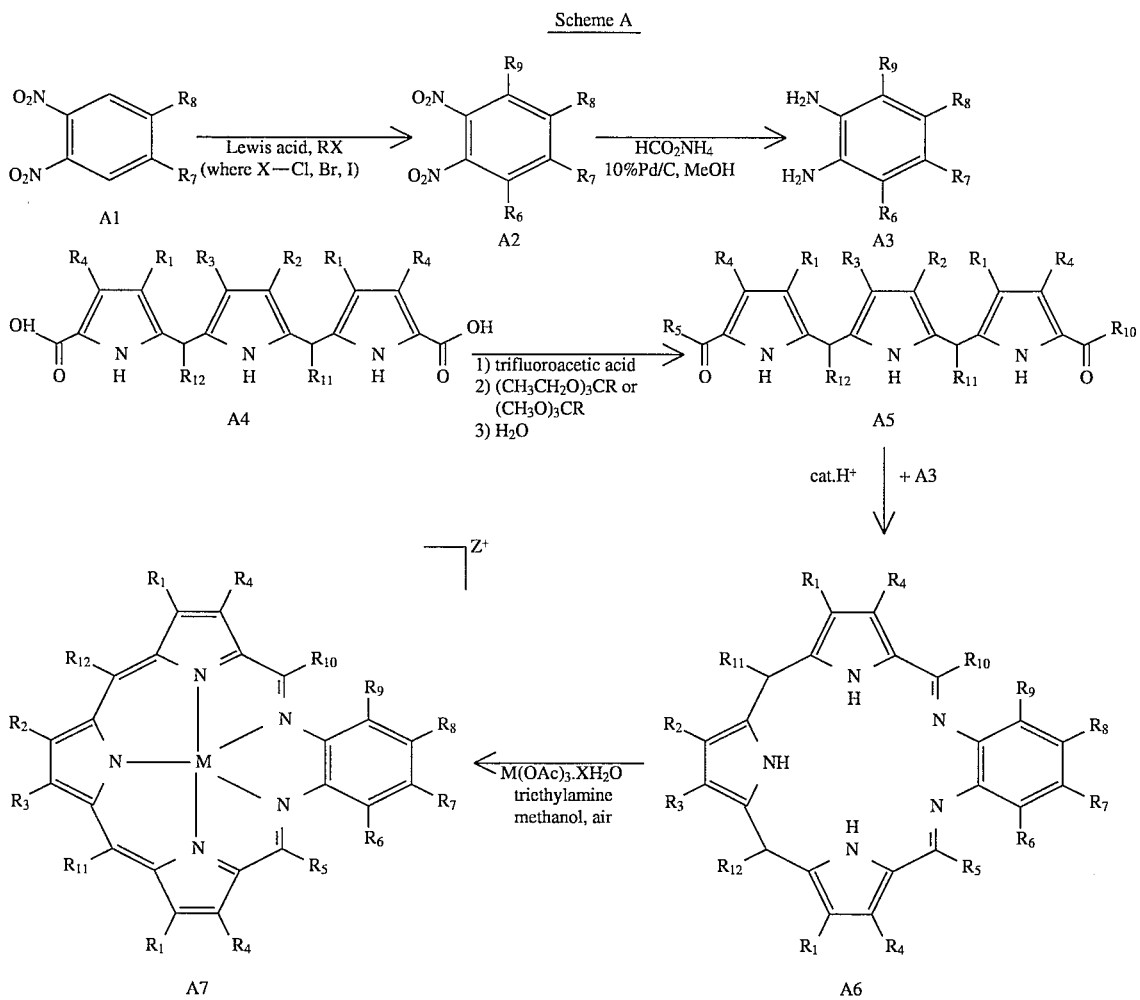

Scheme A

Tripyrrane ketone A5: An example of the synthesis of a precursor to a tripyrrane ketone, the 2,5-bis[(3-(3-hydroxypropyl)-carboxyl-4-methylpyrrol-2-yl)methyl]-3,4-diethylpyrrole F5, Scheme F, was presented in prior application, U.S. Ser. No. 08/135,118, incorporated by reference herein.

In this example, $R_1$ is 3-hydroxypropyl, $R_2$ and $R_3$ are ethyl and $R_4$ is methyl.

The synthesis of compound F5 provides teachings for the synthesis of A4, precursor to tripyrrane ketone A5 as shown in Scheme F and described herein.

Scheme F

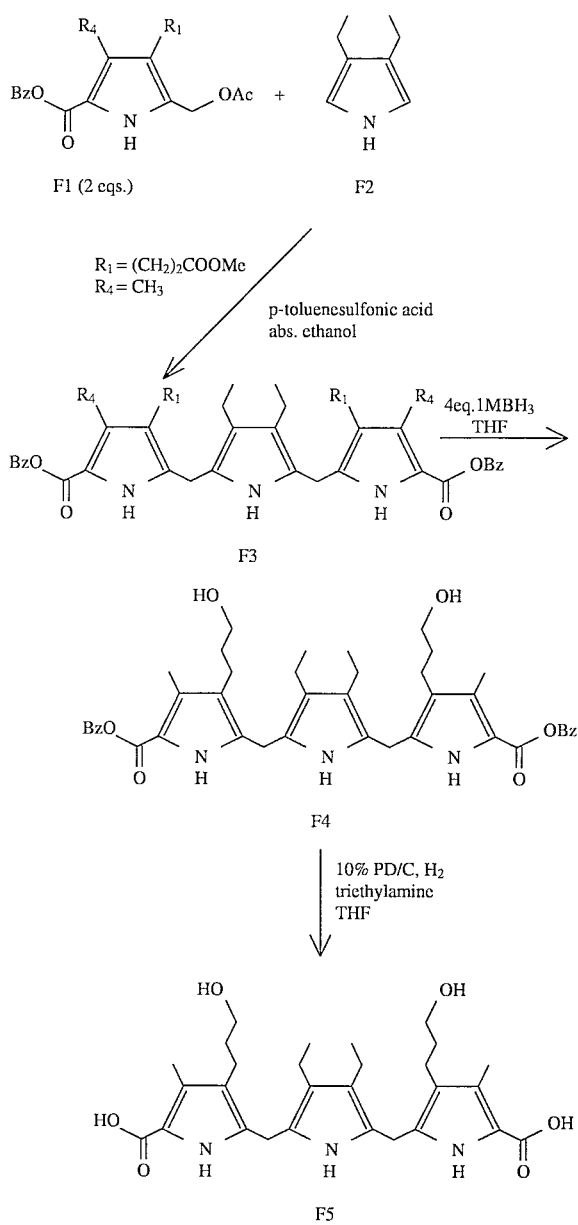

2,5-Bis[(5-benzyloxycarbonyl-4-methyl-3-methoxycarbonylethylpyrrol-2-yl)methyl]-3,4-diethylpyrrole. F3, Scheme F. In a 500 mL round bottom flask was placed 250 mL of ethanol from an unopened bottle which is purged with dry nitrogen for ten minutes. 3,4-Diethylpyrrole F2 (1.29 g, 0.01 mol) and 2-acetoxymethyl-5-benzyloxycarbonyl-4-methyl-3-methoxycarbonylethylpyrrole F1 (7.83 g, 0.02 mol) were added and the mixture heated until all of the pyrroles dissolved. p-Toluenesulfonic acid (65 mg) was added and the reaction temperature maintained at 60° C. The reaction slowly changed color from a clear yellow to a dark red with the product precipitating out of the solution as the reaction progressed. After ten hours the reaction was cooled to room temperature, the volume reduced to one half on a rotary evaporator, and then placed in the freezer for several hours. The product was collected by filtration, washed with a small amount of cold ethanol to afford 4.61 g of an off-white fine powder (61%): $^1$H NMR (CDCl$_3$, 250 MHz): δ1.14 (6H, t, CH$_2$CH$_3$), 2.23 (6H, s, pyrrole-CH$_3$), 2.31 (4H, t, CH$_2$CH$_2$CO$_2$CH$_3$), 2.50 (4H, q, CH$_2$CH$_3$), 2.64 (4H, t, CH$_2$CH$_2$CO$_2$CH$_3$), 3.60 (10H, br s, CH$_3$CO$_2$— and (pyrrole)$_2$-CH$_2$), 4.44 (4H, br s, C$_6$H$_5$CH$_2$), 6.99–7.02 (4H, m, aromatic), 7.22–7.26 (6H, m, aromatic), 8.72 (1H, s, NH), 10.88 (2H, br s, NH); $^{13}$C NMR (CDCl$_3$, 250 MHz): δ10.97, 16.78, 17.71, 19.40, 22.07, 35.09, 51.46, 65.32, 117.37, 119.34, 122.14, 126.58, 126.79, 127.36, 128.19, 133.55, 136.62, 162.35, 173.49; CI MS (M+H)+750; HRMS 749.3676 (calc. for C$_{44}$H$_{51}$N$_3$O$_8$: 749.3676).

A synthetic scheme is presented in Scheme G for the attachment of an ester, a carboxyl and a tertiary amide as R$_2$ and R$_3$ substituents. The synthesis of compound G1 is described in Kaesler et al. (1983).

Scheme G

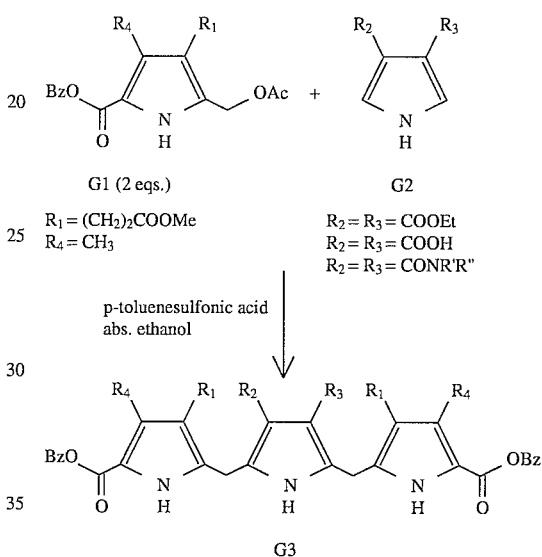

2,5-Bis[(5-benzyloxycarbonyl-3-(3-hydroxypropyl)-4-methylpyrrol-2-yl)methyl]-3,4-diethylpyrrole. F4, Scheme F. 2,5-Bis[(5-benzyloxycarbonyl-4-methyl-3-methoxycarbonylethylpyrrol-2-yl)methyl]-3,4-diethylpyrrole F3 (5.00 g, 0.007 mol) was placed in a three necked 100 mL round bottom flask and vacuum dried for at least 30 minutes. The flask was equipped with a thermometer, an addition funnel, a nitrogen inlet tube, and a magnetic stir bar. After the tripyrrane was partially dissolved into 10 mL of dry THF, 29 mL of borane (1M BH$_3$ in THF) was added dropwise with stirring. The reaction became mildly exothermic and was cooled with a cool water bath. The tripyrrane slowly dissolved to form a homogeneous orange solution which turned to a bright fluorescent orange color as the reaction went to completion. After stirring the reaction for one hour at room temperature, the reaction was quenched by adding methanol dropwise until the vigorous effervescence ceased. The solvents were removed under reduced pressure and the resulting white solid redissolved into CH$_2$Cl$_2$. The tripyrrane was washed three times with 0.5M HCl (200 mL total), dried over anhydrous K$_2$CO$_3$, filtered, and the CH$_2$Cl$_2$ removed under reduced pressure until crystals of the tripyrrane just started to form. Hexanes (50 Ml) was added and the tripyrrane allowed to crystallize in the freezer for several hours. The product was filtered and again recrystallized from CH$_2$Cl$_2$/ethanol. The product was collected by filtration and vacuum dried to yield 3.69 g of an orangish white solid (76%): mp 172°–173° C.; $^1$H NMR (CDCl$_3$, 300 MHz): δ1.11 (6H, t, CH$_2$CH$_3$), 1.57 (4H, p, CH$_2$CH$_2$CH$_2$OH), 2.23

(6H, s, pyrrole-CH$_3$), 2.39–2.49 (8H, m, CH$_2$CH$_3$ and CH$_2$CH$_2$CH$_2$OH), 3.50 (4H, t, CH$_2$CH$_2$CH$_2$OH), 3.66 (4H, s, (pyrrole)$_2$-CH$_2$), 4.83 (4H, s, C$_6$H$_5$–CH$_2$), 7.17–7.20 (4H, m, aromatic), 7.25–7.30 (6H, m, aromatic), 8.64 (1H, s, NH), 9.92 (2H, s, NH); $^{13}$C NMR (CDCl$_3$, 300 MHz): δ10.97, 16.72, 17.68, 20.00, 22.38, 33.22, 62.01, 65.43, 117.20, 119.75, 120.72, 122.24, 127.23, 127.62, 128.30, 132.95, 136.60, 162.13; FAB MS (M$^+$) 693.

2,5-Bis[(3-(3-hydroxypropyl)-5-carboxyl-4-methyl pyrrol-2-yl) methyl]-3,4-diethylpyrrole F5, Scheme F. 2,5-Bis [(3-(3-hydroxypropyl-5-benzyloxycarbonyl-4-methylpyrrol-2-yl)methyl]-3,4-diethylpyrrole F4 (15.0 g, 0.02 mol) was placed in a 1 L round bottom flask and dried in vacuo for ca. 30 min. The tripyrrane was dissolved in dry THF (600 mL) with triethylamine (10 drops) and 10% Pd on carbon (600 mg) and the reaction was stirred at room temperature under one atmosphere of H$_2$. After 15 h, the suspension was filtered through celite to remove the catalyst and the resulting clear solution was concentrated under reduced pressure to yield a light pink solid. This material, obtained in near quantitative yield, was taken on to the next step without further purification.

A carboxyl tripyrrane A4 (a specific example presented as F5 in Scheme F) (0.02 mol) is placed in a 250 mL round bottom flask and dried in vacuo for ca. 1 h. At room temperature under nitrogen, trifluoroacetic acid (31 mL, 0.40 mol) is added dropwise via syringe. The tripyrrane dissolves with visible evolution of CO$_2$ to form a homogeneous yellow solution. The reaction is stirred at room temperature for ca. 15 min, then cooled to 0° C. using a water/ice bath. A triethyl-ortho-ester (or trimethyl-orthoester, ca. 18 eq) is added to the reaction mixture dropwise with stirring after which the reaction is stirred for an additional 15 minutes at 0° C. If the ester is acetate, then a methyl group would be attached, propionate would attach an ethyl group, for example. The reaction is warmed to room temperature and 100 mL of water added dropwise. After stirring the resulting two phase mixture for ca. 30 minutes, the reaction mixture is extracted three times with CH$_2$Cl$_2$. The CH$_2$Cl$_2$ extracts are combined and washed three times with 1M aq. NaHCO$_3$, once with water, dried over anhydrous sodium sulfate, filtered, and the solvent removed under reduced pressure. The resulting solid is recrystallized from CH$_2$Cl$_2$/hexanes.

Substituted ortho-phenylenediamine: The synthesis of an ortho-phenylenediamine substituted at the 4 and 5 positions is described in U.S. Pat. No. 5,252,720 and application Ser. No. 08/135,118.

Texaphyrin macrocycles having a free carboxyl or a free amino group for further derivatization on the benzene ring portion of the molecule may be synthesized by replacing ortho-phenylenediamine with 3,4-diaminobenzoic acid or 3,4-diaminoaniline. One skilled in the art of organic synthesis would realize in light of the present disclosure that other substituted 1,2-o-phenylenediamines may be used as a precursor, e.g., a 1,2-o-phenylenediamine that is differentially substituted in the 4 and 5 positions. This substitution may be the result of different functionalities being present or specific protection and standard organic and/or biochemical transformations having been carried out. Such macrocycles can be further functionalized to derivatives having an antibody, oligonucleotide, protein, peptide, sapphyrin and the like on one position of the B portion of the molecule.

Synthesis of A3, Scheme A: Compound A1 of Scheme A (a 1,2-dialkyl-4,5-dinitrobenzene) is reacted with an alkyl halide where the halide is chloride, bromide or iodide in the presence of a Lewis acid such as AlCl$_3$, for example. The 3 and 6 positions of the phenyl ring are derivatized with the alkyl group to form compound A2. A mixture of reactants having a single halide and different alkyl groups may be used to generate different alkyl derivatives at the 3 and 6 positions. The yield of a particular product would be lower in this case.

A diamine A3 (Scheme A) is obtained by reduction of the corresponding substituted dinitrobenzene (A2, Scheme A) with hydrazine hydrate (1 mL) and 10% palladium on carbon (50 mg) in 40 mL refluxing absolute methanol. The resulting suspension may bubble for approximately 15–20 minutes and then turn colorless after 1 hour. At this point the reduction is complete as verified by TLC. The reaction solution is hot filtered through celite into a dry flask, covered with aluminum foil, and then concentrated to an oil. The diamine is taken to the next step without further purification. Ammonium formate in the presence of palladium (10% on carbon) catalyst may act as a mild, inexpensive and safe alternative to hydrazine hydrate in the above reaction and would be used, for example, when sensitive groups such as amide are present at other positions of the molecule.

Condensation of a tripyrrane ketone and a substituted ortho-phenylenediamine to form a nonaromatic texaphyrin having substituents at the 2, 7, 12, 15, 18 and/or 21 position(s): A tripyrrane ketone and a substituted ortho-phenylenediamine having substituents at the 3 and/or 6 position(s) are placed in a 2 L round bottom flask with 1000 mL of toluene and 200 mL of methanol. The solvents are purged with nitrogen prior to use. Concentrated HCl (0.5 mL) is added and the reaction heated to reflux under nitrogen. After 5 h the reaction is cooled to room temperature and the solvents removed under reduced pressure until the product precipitates out of solution. The remainder of the solvent is decanted off and the macrocycle is dried in vacuo. The product is recrystallized from methanol/diethylether and characterized by $^1$H NMR and $^{13}$C NMR.

Condensation of a diformyltripyrrole and a substituted ortho-phenylenediamine yields a nonaromatic texaphyrin having substituents in the 15, 16, 17 or 18 positions.

General procedure for the synthesis of a metal complex of texaphyrin (A7, Scheme A). One equivalent of the hydrochloride salt of the macrocycle A6, 1.5 equivalents of the M(OAc$_3$)$_3$·XH$_2$O metal salt (where M=metal ion), and triethylamine (ca. 1 mL) are mixed together in methanol and heated to reflux under air. After completion of the reaction (as judged by the UV/vis spectrum of the reaction mixture), the solution is cooled to room temperature, the solvent is removed under reduced pressure and the crude complex dried in vacuo for several hours. A solution of dichloromethane/methanol (99:1 v/v) is added to the crude complex and the suspension is sonicated a few min. The suspension is filtered in order to remove impurities in the filtrate (incomplete oxidation products and excess triethylamine). The resulting solid is dissolved in methanol and then chloroform is added to reduce the polarity of the mixture (1:2 v/v). This solution is filtered through celite and loaded on a (pre-treated/pre-washed 1M NaNO$_3$) neutral alumina column (10 cm). The column is first eluted with a 1:10 (v/v) methanol/chloroform solution by gravity to remove any impurity. The metal complex is then obtained by eluting the column with chloroform containing increasing amounts of methanol (20–50%). The purified lanthanide(III) texaphyrin complex is recrystallized by dissolving the complex in methanol/chloroform and carefully layering the solution with a small amount of methanol, then with diethylether. The layered solution is kept at room temperature in the dark for a few days. The texaphyrin metal complex is recrystallized twice for analytically pure measurements and characterizations.

Alternatively, the crude metal complex may be isolated by mixing the complex with an aqueous solution of a salt at a temperature above the freezing point of the resulting mixture, and then recovering the precipitated texaphyrin from the mixture. The salt can be any salt that is soluble in water or a water/organic solvent mixture and does not cause transmetallation of the texaphyrin metal complex.

The texaphyrin metal complex may alternatively be purified by dissolving the complex in water and methanol, and acid-washed zeolites (such as LZY-54 zeolite) are then added to the solution. The mixture is agitated for a period of time and is then filtered to remove the zeolites. This procedure may be repeated 2 or more times until significantly all of the free metal ion is removed.

Lanthanum(III), Cerium(III), Praseodymium(III), Neodymium(III), Samarium(III), Europium(III), Gadolinium (III), Terbium(III), Dysprosium(III), Holmium(III), Erbium(III), Thulium(III), Ytterbium(III), Lutetium(III) complexes of texaphyrin: The hydrochloride salt of macrocycle A6 (0.407 mmol), and one of the following lanthanide salts:

$La(OAc_3)_3 \cdot 6H_2O$ (0.814 mmol), $Ce(OAc_3)_3 6H_2O$ (0.611 mmol), $Pr(OAc_3)_3 \cdot 5H_2O$ (0.611 mmol), $Nd(OAc_3)_3 \cdot 6H_2O$ (0.611 mmol), $Sm(OAc_3)_3 \cdot 5H_2O$ (0.611 mmol), $Eu(OAc_3)_3 \cdot 5H_2O$ (0.65 mmol), $Gd(OAc_3)_3 \cdot 5H_2O$ (1.5 mmol), $Tb(OAc_3)_3 \cdot 6H_2O$ (0.611 mmol), $Dy(OAc_3)_3 \cdot 5H_2O$ (0.611 mmol), $Ho(OAc_3)_3 \cdot 5H_2O$ (0.611 mmol), $Er(OAc_3)_3 \cdot 5H_2O$ (0.611 mmol), $Tm(OAc_3)_3 \cdot 5H_2O$ (0.611 mmol), $Yb(OAc_3)_3 \cdot 5H_2O$ (0.611 mmol), or $Lu(OAc_3)_3 \cdot H_2O$ (0.611 mmol), together with TBANO$_3$ (1.0 mmol) and triethylamine (ca. 0.5 mL) in 350 mL methanol are heated to reflux under air for 5–24 h. The workup uses the general procedure outlined above. The thulium and lutetium complexes may be more difficult to purify due to their lower solubility in methanol/chloroform solutions, which leads to a lower yield.

EXAMPLE 2

Synthesis of Compounds B4, C5 and D5.

Ortho-phenylenediamine compounds having substituents bound to the phenyl ring via an oxygen are prepared as indicated in Schemes B and C.

Scheme B

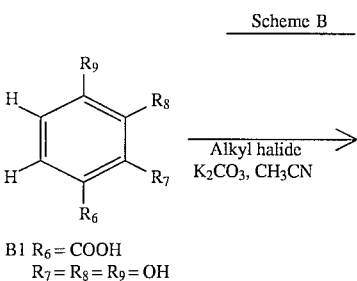

B1 $R_6$ = COOH
$R_7 = R_8 = R_9$ = OH

-continued
Scheme B

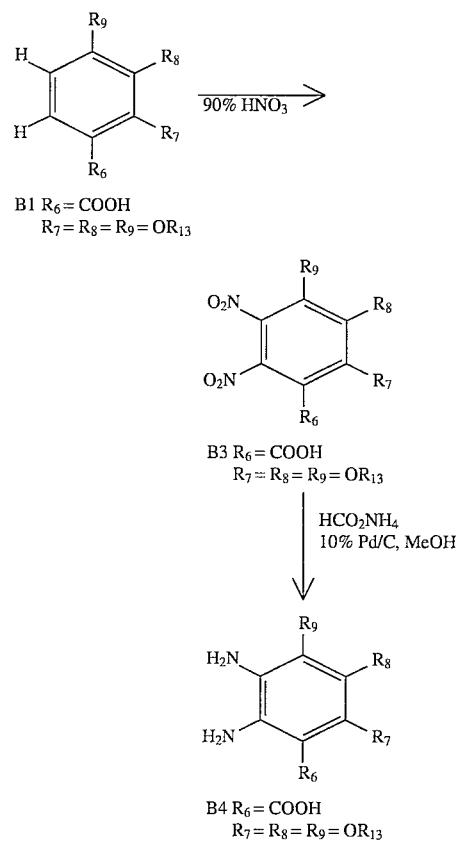

B1 $R_6$ = COOH
$R_7 = R_8 = R_9 = OR_{13}$

B3 $R_6$ = COOH
$R_7 = R_8 = R_9 = OR_{13}$

B4 $R_6$ = COOH
$R_7 = R_8 = R_9 = OR_{13}$

Scheme C

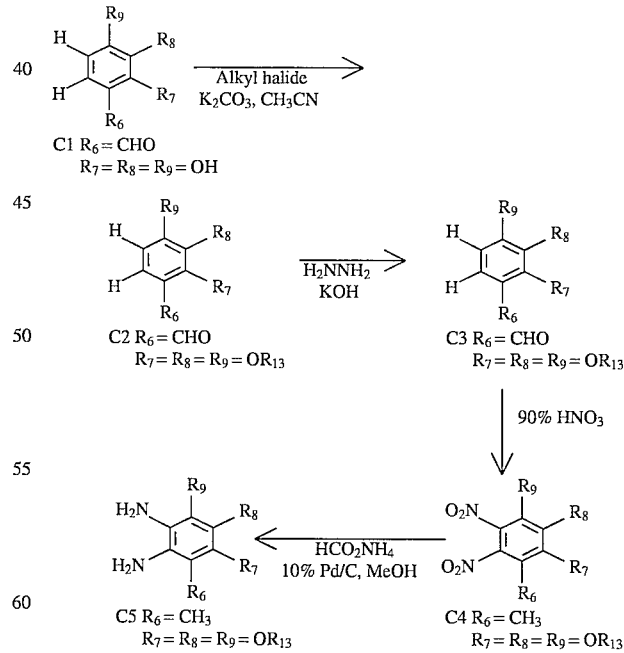

C1 $R_6$ = CHO
$R_7 = R_8 = R_9$ = OH

C2 $R_6$ = CHO
$R_7 = R_8 = R_9 = OR_{13}$

C3 $R_6$ = CHO
$R_7 = R_8 = R_9 = OR_{13}$

C5 $R_6$ = CH$_3$
$R_7 = R_8 = R_9 = OR_{13}$

C4 $R_6$ = CH$_3$
$R_7 = R_8 = R_9 = OR_{13}$ 2,3,4-Trihydroxybenzoic acid B1, is reacted with an alkyl halide where the halide is chloride, bromide, or iodide in the presence of potassium carbonate and acetonitrile to form a trialkoxy derivative B2. The alkyl group of the halide may be a primary or secondary alkyl having one or more hydroxy, alkoxy, carboxy, ester, amine, amide or protected amine substituents at positions at least one carbon removed from the site of halide attachment. These alkyl groups may be unsubstituted, singly or multiply functionalized. They may be branched or unbranched. Preferred alkyl groups are methyl, hydroxypropyl or methoxy(ethoxy)$_n$ethoxy (n=1–100; a polyethylene glycol substituent). Compound B2 is reacted with 90% nitric acid to form the dinitro derivative B3 which is then reacted with either hydrazine hydrate or ammonium formate and 10% palladium on carbon in methanol to form compound B4.

In a similar synthesis, starting with 2,3,4-trihydroxybenzaldehyde C1 (Scheme C), reduction of the trialkoxy derivative C2 with hydrazine in KOH results in a methyl derivative at the $R_6$ position to form 1,2,3-trialkoxy-4-methylbenzene C3. The diamine is formed as depicted in Scheme B and described above.

Scheme D shows the formation of a tertiary amine at the $R_6$ position. The starting material is 2,3,4-trihydroxybenzoic acid (D1). Compound D3 (B3) is treated with an amine component in 1,3-dicyclohexylcarbodiimide and dimethylformamide to form D4 having an amide linkage. Alternative coupling reagents include 1,1'-carbonyldiimidazole (CDI) or ECC. Reduction as described above yields the diamine for condensation with a tripyrrane ketone.

Scheme D

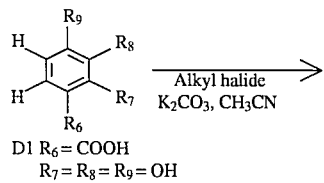

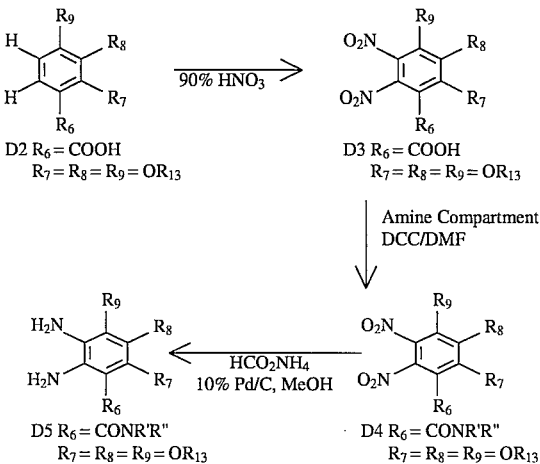

EXAMPLE 3

Synthesis of a T2B4 Texaphyrin

Scheme E, parts 1 and 2, shows the synthesis of a lanthanide metal complex of a T2B4 texaphyrin. A diformyltripyrrole E5 is condensed with a substituted ortho-phenylenediamine E4 to form the nonaromatic precursor E6. The synthesis of the substituted ortho-phenylenediamine E4 was described in example 2 and the diformyltripyrrole was described in U.S. Pat. No. 5,252,720. In this example, R' may be polyethylene glycol (PEG) where the number of repeating ethoxy units may be as many as 200, a saccharide, a polyhydroxy substituent or the like. R may be methoxy, methyl or hydrogen.

Scheme E

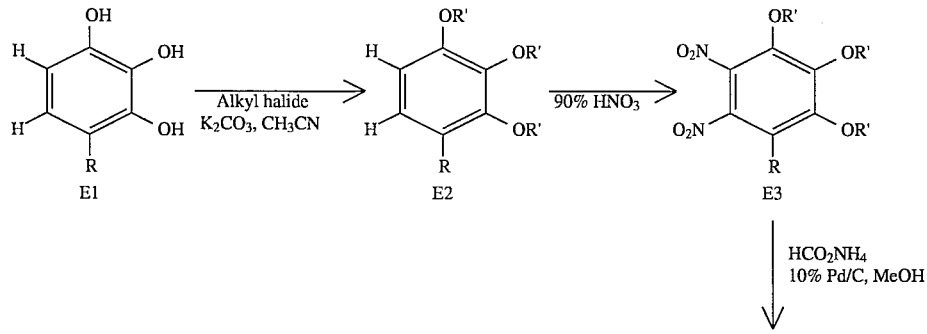

-continued
Scheme E

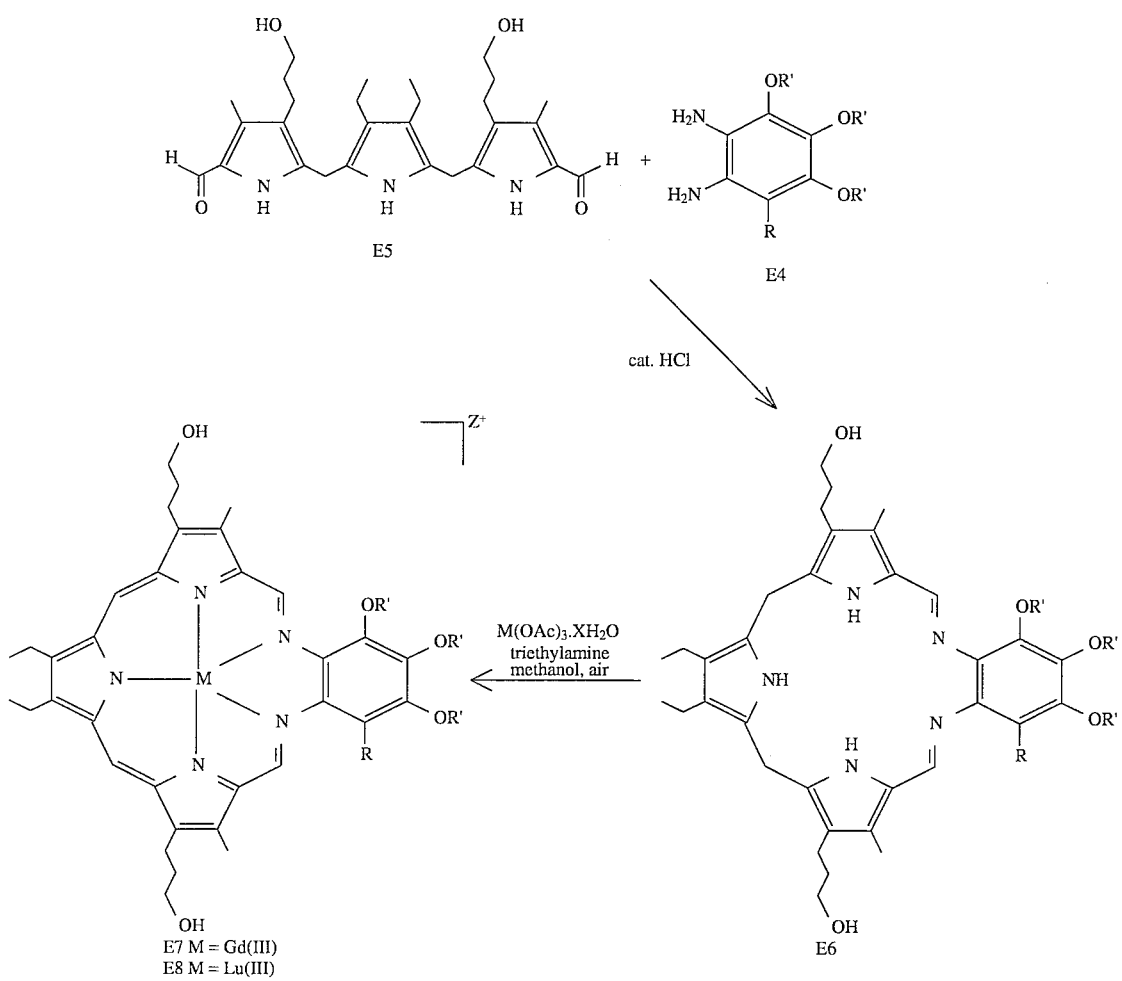

EXAMPLE 4

Synthesis of a Tripyrrane Having Meso-substituents

Scheme A, parts 1 and 2, refers to the structure of a metallotexaphyrin with substituents in the 2 and 7 positions (meso-positions). Texaphyrin macrocycles having meso-substitution on the periphery of the aromatic macrocycle may be synthesized by first preparing new methylene-functionalized tyripyrrane dialdehydes described in Scheme I, parts 1 and 2. One skilled in the art of organic synthesis would realize in light of the present disclosure that a variety of 1,2-o-phenylenediamines may be used to react with these new functionalized tripyrranes. The organic synthesis required for the various transformations illustrated in Scheme I is derived from classic pyrrole/porphyrin chemistry.

Synthesis of I3, Scheme I, part 1: Pyrrole I1 (readily available from Aldrich Chemical Co., Milwaukee, Wis.) of Scheme I is reacted with sulfuryl chloride in dichloromethane, followed by hydrolysis with sodium acetate, and acidification to afford the acid pyrrole, I2 (see A. R. Battersby et al., *J.C.S. Perkin I,* 1976, 1008). Decarboxylation via trifluoroacetic acid yields I3 (see M. J. Cyr, Ph.D. Dissertation, University of Texas at Austin, 1992).

Scheme I

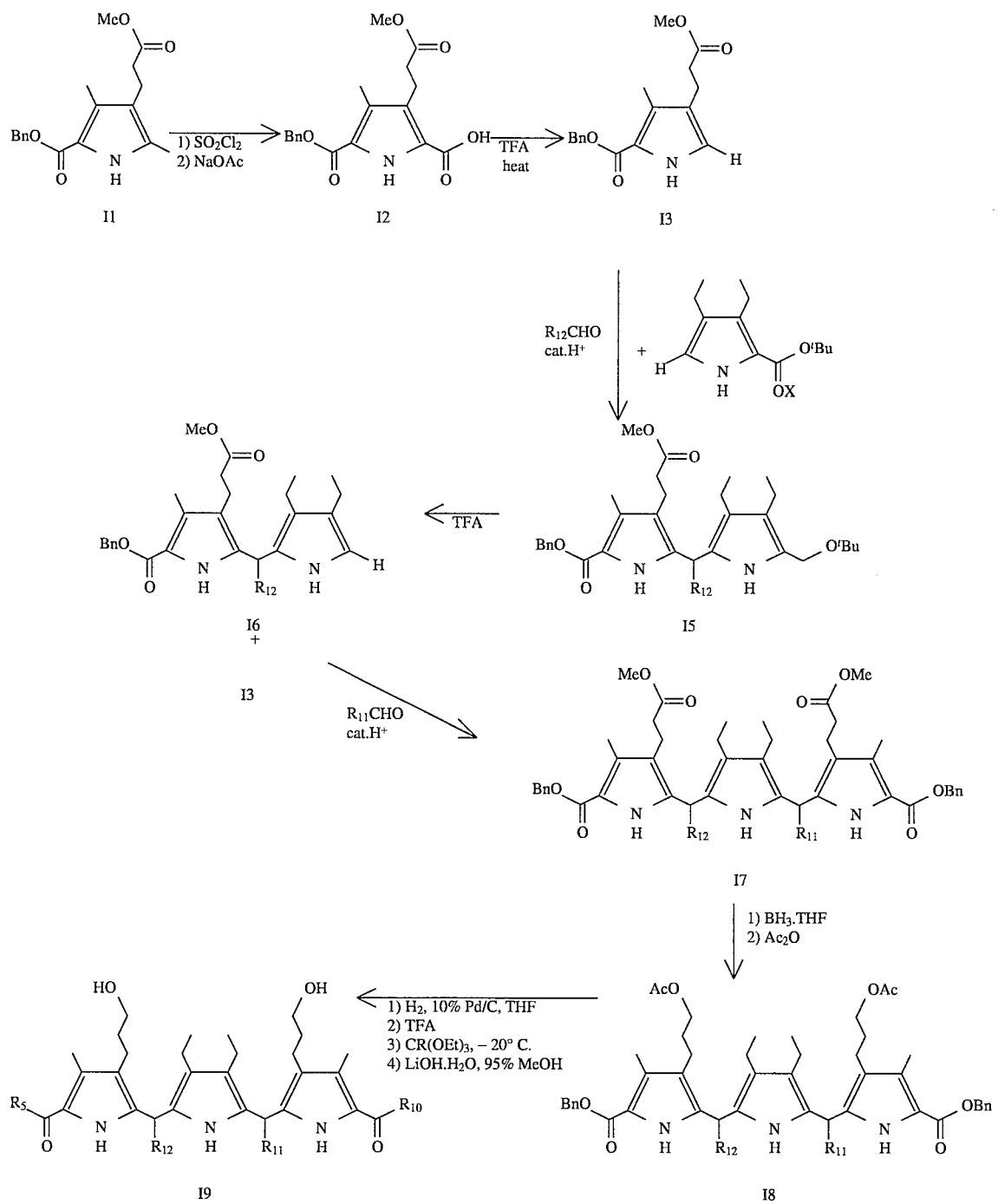

Synthesis of I5. The acid-catalyzed condensation between compound I3 and the t-butylester derived pyrrole I4 (pyrrole I4 is described in D. H. R. Barton and S. Zard, *J.C.S. Chem. Commun.*, 1985, 1098–1100), in the presence of an aldehyde ($R_{12}$=alkyl, aryl, etc.) will afford a mixture of three dipyrromethanes. The desired mixed-ester derived dipyrromethane I5 is obtained by column chromatography. The preparation of dipyrromethanes is well-documented in the literature (see, Sessler et al., *J. Org. Chem.*, 1986, 51, 2838).

Synthesis of I7. The t-butylester of compound I5 is selectively deprotected and decarboxylated via trifluoroacetic acid and subsequently condensed via acid-catalysis with pyrrole I3 in the presence of an aldehyde ($R_{11}$=alkyl, aryl, etc.) to afford the desired tripyrrane I7.

Synthesis of the diformyl tripyrrane I9. With compound I7 in hand, the tripyrrane is transformed to the desired diformyl tripyrrane I9 ($R_5$=H) by standard organic synthesis reported earlier (U.S. Pat. No. 5,252,720). Compound I7 is reduced by borane/THF, followed by acetylation via acetic anhydride or acetyl chloride to afford tripyrrane I8. At this point, debenzylation of I8, followed by subsequent Clezy formylation of the intermediate, and basic hydrolysis with lithium hydroxide, provides tripyrrane I9.

Tripyrrane I9 may then be condensed with an orthophenylenediamine to construct a texaphyrin macrocycle as depicted in Scheme A. Substituents in these meso-positions are expected to further stabilize the macrocycle.

EXAMPLE 5

2,5-Bis[(3-acetoxypropyl-5-benzoyl-4-methylpyrro-2-yl) methyl]-3,4-diethylpyrrole (J2). 2,5-Bis[(3-acetoxypropyl-5-carboxyl-4-methylpyrrol-2-yl)methyl]-3,4-diethylpyrrole J1 (1.00 g, 1.67 mmol) was placed in a 100 mL three-neck round-bottom flask and dried under high vacuum for ca. 1 hr. The round-bottom flask was equipped with an argon inlet line and for magnetic stirring. At room temperature under argon, $CH_2Cl_2$ (10 mL) was added to the flask and the resulting mixture stirred to form a suspension. Trifluoroacetic acid (2.7 mL) was then added all at once to the suspension. The tripyrrane dissolved to form a light orange solution. The reaction was stirred at room temperature under argon for ca. 45 min, after which it was cooled to 0° C. using an ice/water bath. Triethylorthobenzoate (3.8 mL) was added dropwise to the reaction with stirring over a two minute period under a flow of argon. The reaction was stirred for 40 min at 0° C. then allowed to warm to room temperature over 20 min. Water (20 mL) was added to the reaction and stirring continued for another 2 hr. Transferred reaction to a separatory funnel, separated and discarded the upper aqueous phase, and basified the lower organic layer with sat. aqueous $NaHCO_3$ (Caution: gas evolution and frothing occurs). Separated the two layers and washed the organic phase once with sat. aqueous $NaHCO_3$ and once with water. Dried organic phase over anhydrous $MgSO_4$, filtered off the drying agent, removed the solvent under reduced pressure, and dried the resulting orange-red oil under high vacuum overnight. The oil was dissolved into a minimum amount of $CH_2Cl_2$ (5–10 mL), the solution layered with hexanes (ca. 50 mL), and the tripyrrane allowed to crystallize at −20° C. The product was collected by filtration and dried under high vacuum to yield 1.06 grams of a tan solid (J2) (88%). $^1$H NMR ($CDCl_3$, 300 MHz): δ1.06 (6H, t, $CH_2CH_3$), 1.67 (4H, p, $CH_2CH_2CH_2OAc$), 1.81 (6H, s, $CH_3CO_2$—), 2.02 (6H, s, pyrr-$CH_3$), 2.37–2.44 (8H, m, $CH_2CH_3$ and $CH_2CH_2CH_2OAc$), 3.71 (4H, s, $(pyrr)_2$-$CH_2$), 3.99 (4H, t, $CH_2CH_2CH_2OAc$), 7.29–7.48 (10H, m, aromatic), 9.16 (1H, s, NH), 9.66 (2H, s, NH); $^{13}$C NMR ($CDCl_3$): δ11.8, 16.4, 17.7, 20.1, 20.9, 22.7, 29.1, 63.9, 120.9, 121.5, 127.3, 128.1, 128.2, 129.1, 130.8, 135.6, 140.1, 171.3, 185.7; FAB MS, M$^+$: m/e 717.

4,5-Diethyl-9,24-bis(3-hydroxypropyl)-16,17-dimethoxy-10,23-diemthyl-1 2,21-diphenyl-13,20,25,26,27-pentaazapentacyclo-[20.2.1.1$^{3,6}$.1$^{8,11}$.0$^{14,19}$]heptacosa-3,5,8,10,12,14,16,18,20,22,24-undecaene (J6).

2,5-Bis[(3-acetoxypropyl-5-benzoyl-4-methylpyrrol-2-yl)methyl]-3,4-diethylpyrrole J2 (100 mg, 0.14 mmol) and 4,5-dimethoxy-1,2-phenylenediamine J5 (23 mg, 0.14 mmol) were dissolved into 100 mL of absolute methanol under argon. Concentrated HCl (5 drops) was added and the reaction heated at reflux under argon. After heating for 2 days, the reaction was cooled to room temperature and the solvent removed under reduced pressure. The resulting red solid was dissolved into $CH_2Cl_2$ (5 mL), filtered, and the $CH_2Cl_2$ solution layered with hexanes (20 mL). The product was allowed to slowly precipitate out of solution at room temperature overnight. The mother liquor was decanted off and the remaining solid washed with hexanes. After drying the solid under high vacuum, 39 mg of dark red product (J6) was obtained. FAB MS, (M+H)$^+$: m/e 766.

Cadmium(II) complex of 4,5-diethyl-9,24-bis(3-hydroxypropyl)-16,17-dimethoxy-10,23-dimethyl-1 2,21-diphenyl-13,20,25,26,27-pentaazapentacyclo[20.2.1. 1$^{3,6}$.1$^{8,11}$.0$^{14,19}$]-heptacosa-1,3,5,7,9,11(27),12,14(19),15, 17,20, 22(25),23-tridecaene (J8). The protonated form of the macrocycle J6 (11 mg, 0.014 mmol), cadmium(II) chloride (11 mg, 0.06 mmol) and triethylamine (20 mL) in 20 mL of methanol were heated at reflux under air for 2 days. The reaction was cooled to room temperature, the solvent removed under reduced pressure, and the complex dried in vacuo overnight to give the final texaphyrin-Cd(II) metal complex (J8). UV/vis ($CH_3OH$) [λ$_{max}$, nm]: 472.0, 756.0; FAB MS, (M+H)$^+$: m/e 875.

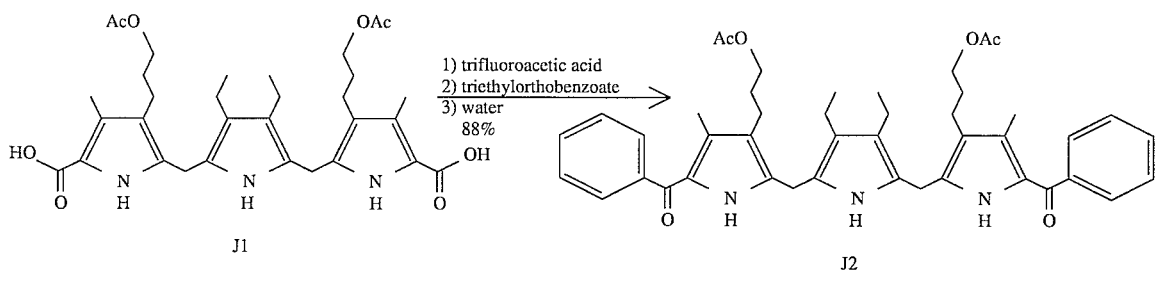

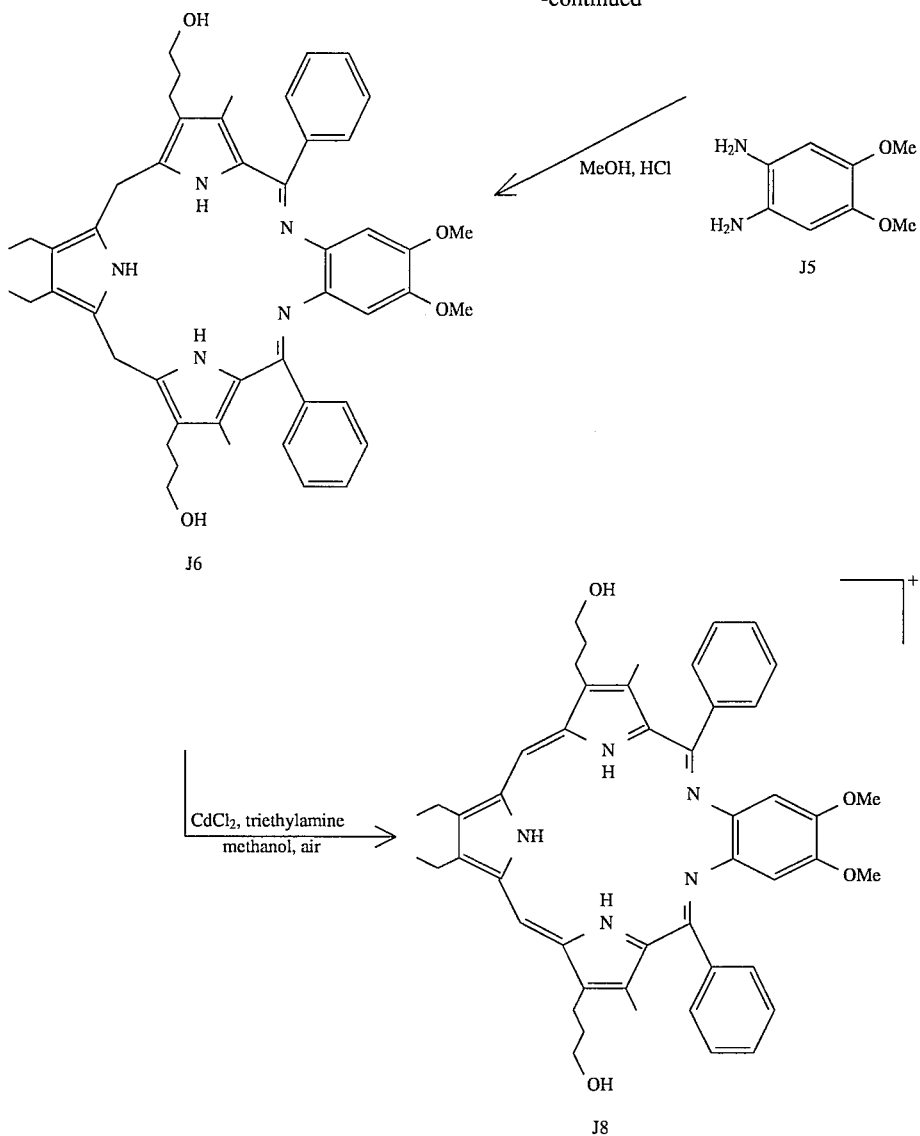

EXAMPLE 6

2,5-bis[(5-benzoyl-3-ethyl-4-methylpyrrol-2-yl)methyl]-3,4-diethylpyrrole (J4). 2,5-Bis[(5-carboxyl-3-ethyl-4-methylpyrrol-2-yl)methyl]-3,4-diethylpyrrole J3 (1.00 g, 2.20 mmol) was placed in a 100 mL three-neck round-bottom flask and dried under high vacuum for 1 hr. The round-bottom flask was equipped with an argon inlet line and for magnetic stirring. At room temperature under argon, $CH_2Cl_2$ (10 mL) was added to the reaction flask and the resulting mixture stirred to form a suspension. Trifluoroacetic acid (3.5 mL) was then added all at once to the suspension. The tripyrrane dissolved to form a yellowish orange solution. The reaction was stirred at room temperature under argon for ca. 35 min, after which it was cooled to 0° C. using an ice/water bath. Triethylorthobenzoate (5.0 mL) was added dropwise to the reaction with stirring over a two minute period under a flow of argon. The reaction was stirred for 40 min at 0° C. then allowed to warm to room temperature over 20 min. Water (20 mL) was added to the reaction and stirring continued for another 1 hr. Transferred reaction to a separatory funnel, separated and discarded the upper aqueous phase, and basified the lower organic layer with sat. aqueous $NaHCO_3$ (30 mL) (Caution: gas evolution and frothing occurs). Separated the two layers and washed the organic phase once with sat. aqueous $NaHCO_3$ and once with water. Dried organic phase over anhydrous $MgSO_4$, filtered off the drying agent, and removed the solvent under reduced pressure to yield a dark oil with some precipitate. The oil and solid were dissolved into a minimum mmount of $CH_2Cl_2$ (5 mL), the solution layered with hexanes (ca. 50 mL), and the product allowed to crystallize at −20° C. The product was collected by filtration, washed with a small amount of hexanes, and dried under high vacuum to yield 0.88 grams of a tan solid (J4) (70%). $^1H$ NMR ($CDCl_3$, 300 MHz): δ0.95 (6H, t, $CH_2CH_3$), 1.05 (6H, t, $CH_2CH_3$), 1.80 (6H, s, pyrr-$CH_3$), 2.32–2.40 (8H, m, $CH_2CH_3$), 3.67 (4H, s, (pyrr)$_2$-$CH_2$), 7.27–7.48 (10H, m, aromatic), 9.27 (1H, s, NH), 9.66 (2H, s, NH); $^{13}C$ NMR ($CDCl_3$): δ11.7, 15.1, 16.3, 17.1, 17.7, 22.8, 120.8, 121.4, 124.8, 127.0, 128.0(6), 128.1(4), 129.2, 130.6, 135.5, 140.2, 185.7; FAB MS, $(M+H)^+$: m/e 574.

4,5,9,24-Tetraethyl-16,17-dimethoxy-10,23-dimethyl-12,21-diphenyl-13,20,25,26,27-pentaazapentacyclo-[20.2.1.1$^{3,6}$.1$^{8,11}$0$^{14,19}$]heptacosa-3,5,8,10,12,14,16,18,20,22,24-undecaene (J7). 2,5-Bis[(5-benzoyl-3-ethyl-4-methylpyrrol-2-yl)methyl]-3,4-diethylpyrrole J4 (101 mg, 0.18 mmol) and 4,5-dimethoxy-1,2-phenylenediamine J5 (30 mg, 0.18 mmol) were dissolved into 200 mL of toluene and 100 mL of absolute methanol. The solvents were sparged with argon for approximately 5 min before the reaction was started. Concentrated HCl (3 drops) was then added and the reaction heated at reflux under an atmosphere of argon. After heating for ca. 2.75 days, the reaction was cooled to room temperature, the solvent removed under reduced pressure and the remaining solid dried in vacuo. The macrocycle was dissolved into $CH_2Cl_2$ (10 mL), filtered, and the $CH_2Cl_2$ solution layered with hexanes (80 mL). The product was allowed to slowly precipitate out of solution at $-20°$ C. overnight. The macrocycle was collected by filtration, dissolved into a minimum amount of ethanol, and the solution layered with hexanes. The macrocycle was allowed to slowly precipitate out of solution at $-20°$ C. for several days. The macrocycle was collected by filtration, washed with a small amount of hexanes, and dried under high vacuum to yield 28 mg of dark red product (J7). FAB MS, $(M+H)^+$: m/e 707.

Macrocycle J7 can be oxidized and metallated to give the corresponding texaphyrin metal complex following the procedures previously described herein.

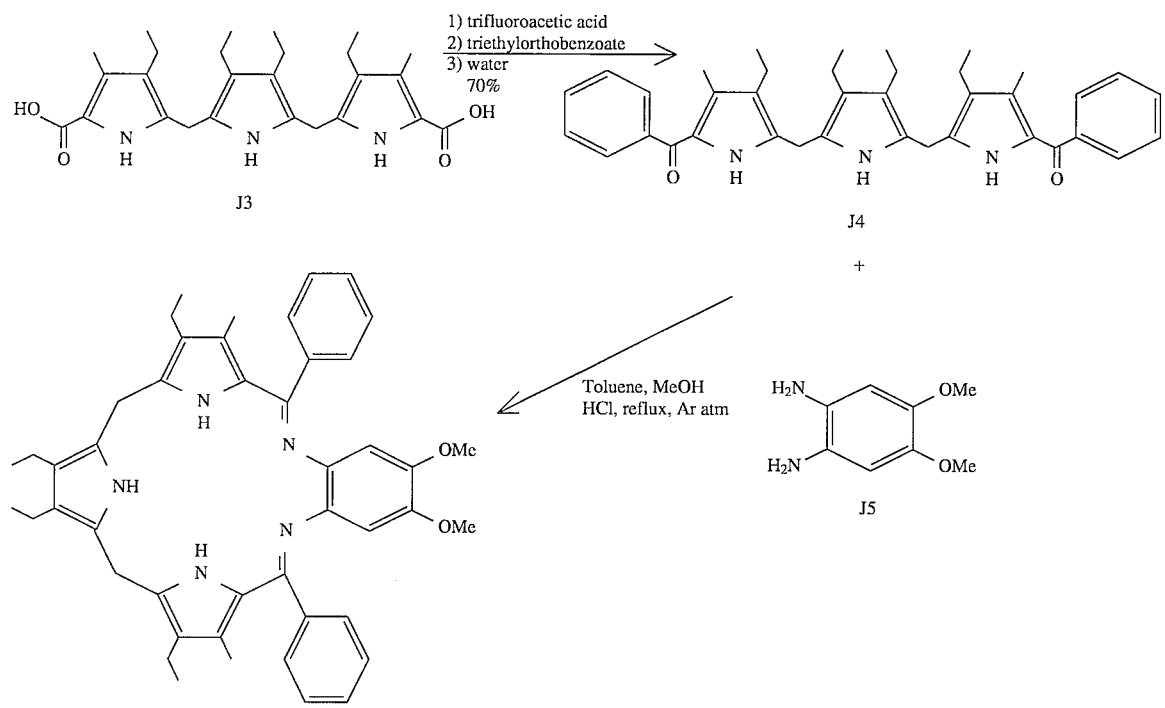

EXAMPLE 7

$R_5$, $R_6$, $R_9$ and/or $R_{10}$ Substituents

Scheme H, parts 1 and 2, shows a synthetic scheme for attaching a nitro group at position $R_6$ or $R_9$.

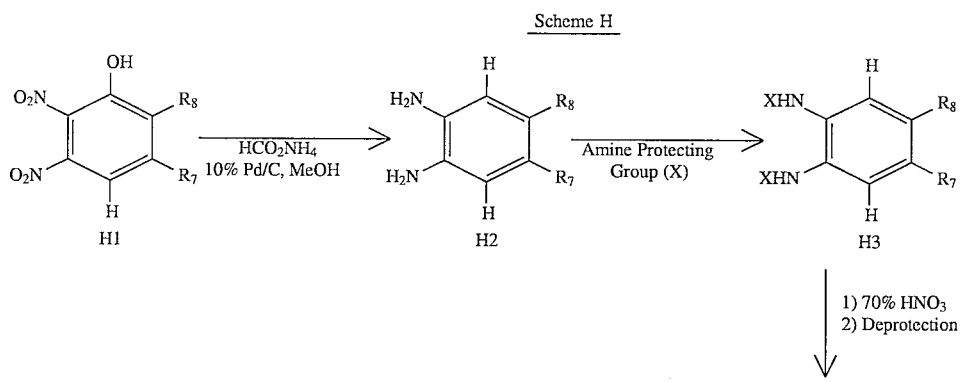

-continued
Scheme H

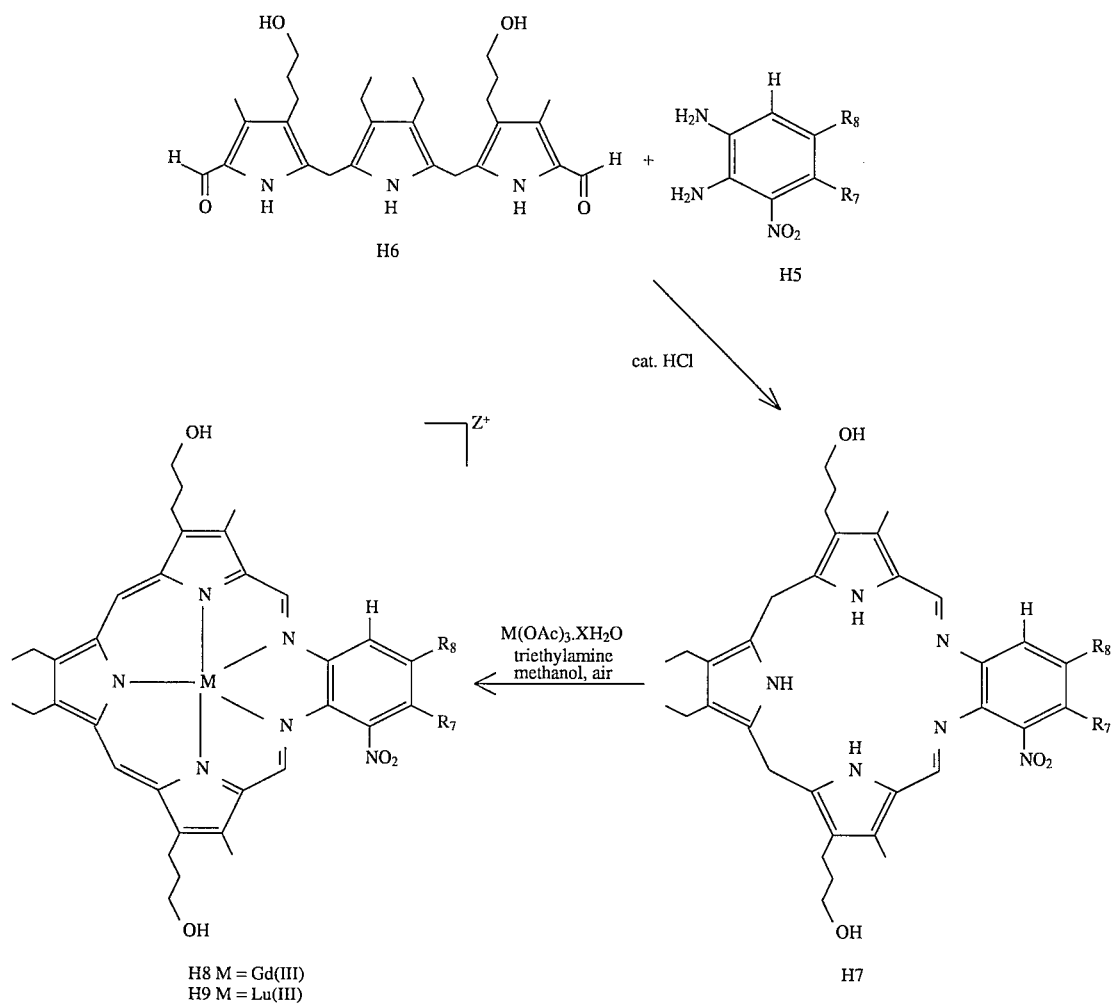

$R_7 = R_8 =$ polyethylene glycol(PEG)$_n$, n = 1–200; saccharide, polyhydroxy

A 1,2-dialkyl-4,5-dinitrobenzene (H1, also A1) is reduced with ammonium formate to the diamino derivative and an amine protecting group is attached before the nitration step. Amine protecting groups include amides such as N-acetyl, and carbamates such as CBZ, for example. An acetyl protecting group is later removed by refluxing in HCl. Protection and deprotection procedures are well known to those of skill in the art in light of the present disclosure (Greene et al. 1991). The deprotected nitro derivative H5 is condensed with a diformyltripyrrane H6 to form a nonaromatic texaphyrin having a nitro group at the 15 position.

A bromine is introduced at the $R_6$ and $R_9$ positions of the macrocycle by reacting 1,2-dialkyl-4,5-dinitrobenzene with bromine in the presence of FeBr$_3$ or AlBr$_3$. The 3 and 6 positions of the phenyl ring are derivatized with bromide and reduction to the amine as described in example 2 prepares the precursor for condensation with a diformyltripyrrole or a tripyrrane ketone.

Preferred texaphyrins having a substituent on the 2, 7, 12, 15, 18 and/or 21 position of the macrocycle are listed in Tables A and B. Substituents $R_1$–$R_6$ are provided in Table A and $R_7$–$R_{12}$ are provided in Table B for a given texaphyrin ("TXP").

TABLE A

Representative Substituents for Texaphyrin Macrocycles A1–A50 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|-----|-------|-------|-------|-------|-------|-------|
| A1  | CH$_2$(CH$_2$)$_2$OH | CH$_2$CH$_3$ | CH$_2$CH$_3$ | CH$_3$ | H | COOH |
| A2  | CH$_2$(CH$_2$)$_2$OH | CH$_2$CH$_3$ | CH$_2$CH$_3$ | CH$_3$ | H | COOH |

TABLE A-continued

Representative Substituents for Texaphyrin Macrocycles A1–A50 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A3 | $CH_2(CH_2)_2OH$ | $CH_2CH_3$ | $CH_2CH_3$ | $CH_3$ | H | $CONHCH—(CH_2OH)_2$ |
| A4 | $CH_2(CH_2)_2OH$ | $CH_2CH_3$ | $CH_2CH_3$ | $CH_3$ | H | $CONHCH—(CH_2OH)_2$ |
| A5 | $CH_2(CH_2)_2OH$ | $CH_2CH_3$ | $CH_2CH_3$ | $CH_3$ | H | H |
| A6 | $CH_2(CH_2)_2OH$ | $CH_2CH_3$ | $CH_2CH_3$ | $CH_3$ | H | $OCH_3$ |
| A7 | $CH_2(CH_2)_2OH$ | $CH_2CH_3$ | $CH_2CH_3$ | $CH_3$ | H | $OCH_3$ |
| A8 | $CH_2(CH_2)_2OH$ | $CH_2CH_3$ | $CH_2CH_3$ | $CH_3$ | H | $OCH_3$ |
| A9 | $CH_2(CH_2)_2OH$ | $CH_2CH_3$ | $CH_2CH_3$ | $CH_3$ | H | $OCH_3$ |
| A10 | $CH_2(CH_2)_2OH$ | $CH_2CH_3$ | $CH_2CH_3$ | $CH_3$ | H | $OCH_3$ |
| A11 | $CH_2(CH_2)_2OH$ | $CH_2CH_3$ | $CH_2CH_3$ | $CH_3$ | H | $OCH_3$ |
| A12 | $CH_2(CH_2)_2OH$ | $CH_2CH_3$ | $CH_2CH_3$ | $CH_3$ | H | $OCH_3$ |
| A13 | $CH_2(CH_2)_2OH$ | $CH_2CH_3$ | $CH_2CH_3$ | $CH_3$ | H | $CH_3$ |
| A14 | $CH_2(CH_2)_2OH$ | $CH_2CH_3$ | $CH_2CH_3$ | $CH_3$ | H | $CH_3$ |
| A15 | $CH_2(CH_2)_2OH$ | $CH_2CH_3$ | $CH_2CH_3$ | $CH_3$ | H | $CH_3$ |
| A16 | $CH_2(CH_2)_2OH$ | $CH_2CH_3$ | $CH_2CH_3$ | $CH_3$ | H | $CH_3$ |
| A17 | $CH_2(CH_2)_2OH$ | $CH_2CH_3$ | $CH_2CH_3$ | $CH_3$ | $CH_3$ | H |
| A18 | $CH_2(CH_2)_2OH$ | $CH_2CH_3$ | $CH_2CH_3$ | $CH_3$ | $CH_3$ | H |
| A19 | $CH_2(CH_2)_2OH$ | $CH_2CH_3$ | $CH_2CH_3$ | $CH_3$ | $CH_3$ | H |
| A20 | $CH_2(CH_2)_2OH$ | $CH_2CH_3$ | $CH_2CH_3$ | $CH_3$ | $CH_3$ | H |
| A21 | $CH_2(CH_2)_2OH$ | $CH_2CH_3$ | $CH_2CH_3$ | $CH_3$ | $CH_3$ | H |
| A22 | $CH_2(CH_2)_2OH$ | $CH_2CH_3$ | $CH_2CH_3$ | $CH_3$ | $CH_3$ | H |
| A23 | $CH_2(CH_2)_2OH$ | $CH_2CH_3$ | $CH_2CH_3$ | $CH_3$ | $CH_3$ | H |
| A24 | $CH_2(CH_2)_2OH$ | $CH_2CH_3$ | $CH_2CH_3$ | $CH_3$ | $CH_3$ | H |
| A25 | $CH_2(CH_2)_2OH$ | $CH_2CH_3$ | $CH_2CH_3$ | $CH_3$ | $CH_3$ | H |
| A26 | $CH_2(CH_2)_2OH$ | $CH_2CH_3$ | $CH_2CH_3$ | $CH_3$ | $CH_3$ | OH |
| A27 | $CH_2(CH_2)_2OH$ | $CH_2CH_3$ | $CH_2CH_3$ | $CH_3$ | $CH_3$ | F |
| A28 | $CH_2(CH_2)_2OH$ | $CH_2CH_3$ | $CH_2CH_3$ | $CH_3$ | $CH_2(CH_2)_6OH$ | H |
| A29 | $CH_2(CH_2)_2OH$ | $CH_2CH_3$ | $CH_2CH_3$ | $CH_3$ | H | Br |
| A30 | $CH_2(CH_2)_2OH$ | $CH_2CH_3$ | $CH_2CH_3$ | $CH_3$ | H | $NO_2$ |
| A31 | $CH_2(CH_2)_2OH$ | $CH_2CH_3$ | $CH_2CH_3$ | $CH_3$ | H | COOH |
| A32 | $CH_2(CH_2)_2OH$ | $CH_2CH_3$ | $CH_2CH_3$ | $CH_3$ | H | $CH_3$ |
| A33 | $CH_2(CH_2)_2OH$ | $CH_2CH_3$ | $CH_2CH_3$ | $CH_3$ | $C_6H_5$ | H |
| A34 | $CH_2(CH_2)_2OH$ | COOH | COOH | $CH_3$ | $CH_2CH_3$ | H |
| A35 | $CH_2(CH_2)_2OH$ | $COOCH_2CH_3$ | $COOCH_2CH_3$ | $CH_3$ | $CH_3$ | H |
| A36 | $CH_2CH_2CON(CH_2CH_2OH)_2$ | $CH_2CH_3$ | $CH_2CH_3$ | $CH_3$ | $CH_3$ | H |
| A37 | $CH_2CH_2ON(CH_3)CH_2—(CHOH)_4CH_2OH$ | $CH_2CH_3$ | $CH_2CH_3$ | $CH_3$ | $CH_3$ | H |
| A38 | $CH_2CH_3$ | $CH_2CH_3$ | $CH_2CH_3$ | $CH_3$ | $CH_2(CH_2)_6OH$ | H |
| A39 | $CH_2(CH_2)_2OH$ | $CH_2CH_3$ | $CH_2CH_3$ | $CH_3$ | $CH_3$ or $CH_2CH_3$ | H |
| A40 | $CH_2(CH_2)_2OH$ | $CH_2CH_3$ | $CH_2CH_3$ | $CH_3$ | $CH_3$ or $CH_2CH_3$ | H |
| A41 | $CH_2(CH_2)_2OH$ | $CH_2CH_3$ | $CH_2CH_3$ | $CH_3$ | $CH_3$ or $CH_2CH_3$ | H |
| A42 | $CH_2(CH_2)_2OH$ | $CH_2CH_3$ | $CH_2CH_3$ | $CH_3$ | $CH_3$ or $CH_2CH_3$ | H |
| A43 | $CH_2(CH_2)_2OH$ | $CH_2CH_3$ | $CH_2CH_3$ | $CH_3$ | $CH_3$ or $CH_2CH_3$ | H |
| A44 | $CH_2(CH_2)_2OH$ | $CH_2CH_3$ | $CH_2CH_3$ | $CH_3$ | $CH_3$ or $CH_2CH_3$ | H |
| A45 | $CH_2(CH_2)_2OH$ | $CH_2CH_3$ | $CH_2CH_3$ | $CH_3$ | $CH_3$ or $CH_2CH_3$ | H |
| A46 | $CH_2(CH_2)_2OH$ | $CH_2CH_3$ | $CH_2CH_3$ | $CH_3$ | $CH_3$ or $CH_2CH_3$ | H |
| A47 | $CH_2(CH_2)_2OH$ | $CH_2CH_3$ | $CH_2CH_3$ | $CH_3$ | $CH_3$ or $CH_2CH_3$ | H |
| A48 | $CH_2(CH_2)_2OH$ | $CH_2CH_3$ | $CH_2CH_3$ | $CH_3$ | $CH_3$ or $CH_2CH_3$ | H |
| A49 | $CH_2(CH_2)_2OH$ | $CH_2CH_3$ | $CH_2CH_3$ | $CH_3$ | $CH_3$ or $CH_2CH_3$ | H |
| A50 | $CH_2(CH_2)_2OH$ | $CH_2CH_3$ | $CH_2CH_3$ | $CH_3$ | $CH_3$ or $CH_2CH_3$ | H |
| A51 | $CH_2(CH_2)_2OH$ | $CH_2CH_3$ | $CH_2CH_3$ | $CH_3$ | H | H |
| A52 | $CH_2(CH_2)_2OH$ | $CH_2CH_3$ | $CH_2CH_3$ | $CH_3$ | H | H |
| A53 | $CH_2(CH_2)_2OH$ | $CH_2CH_3$ | $CH_2CH_3$ | $CH_3$ | H | H |
| A54 | $CH_2(CH_2)_2OH$ | $CH_2CH_3$ | $CH_2CH_3$ | $CH_3$ | H | H |
| A55 | $CH_2(CH_2)_2OH$ | $CH_2CH_3$ | $CH_2CH_3$ | $CH_3$ | $CH_3$ or $CH_2CH_3$ | H |
| A56 | $CH_2(CH_2)_2OH$ | $CH_2CH_3$ | $CH_2CH_3$ | $CH_3$ | $CH_3$ or $CH_2CH_3$ | H |

TABLE B

Representative Substituents for Texaphyrin Macrocycles A1–A50 of the Present Invention.
Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A1 | O(CH$_2$)$_3$OH | O(CH$_2$)$_3$OH | O(CH$_2$)$_3$OH | H | H | H |
| A2 | O(CH$_2$CH$_2$O)$_3$CH$_3$ | O(CH$_2$CH$_2$O)$_3$CH$_3$ | COOH | H | H | H |
| A3 | O(CH$_2$CH$_2$O)$_3$CH$_3$ | O(CH$_2$CH$_2$O)$_3$CH$_3$ | O-saccharide | H | H | H |
| A4 | O(CH$_2$CH$_2$O)$_3$CH$_3$ | O(CH$_2$CH$_2$O)$_3$CH$_3$ | O(CH$_2$CH$_2$O)$_3$CH$_3$ | H | H | H |
| A5 | O(CH$_2$CH$_2$O)$_3$CH$_3$ | O(CH$_2$)$_3$CON-linker oligo | O(CH$_2$CH$_2$O)$_3$CH$_3$ | H | H | H |
| A6 | H | OCH$_2$CON-linker-oligo | OCH$_3$ | H | H | H |
| A7 | H | OCH$_2$CO-poly-L-lysine | OCH$_3$ | H | H | H |
| A8 | H | OCH$_2$CO-estradiol | OCH$_3$ | H | H | H |
| A9 | H | O(CH$_2$CH$_2$O)$_3$CH$_3$ | OCH$_3$ | H | H | H |
| A10 | O(CH$_2$CH$_2$O)$_3$CH$_3$ | O(CH$_2$CH$_2$O)$_3$CH$_3$ | OCH$_3$ | H | H | H |
| A11 | O(CH$_2$CH$_2$O)$_3$CH$_3$ | OCH$_2$CON-linker oligo | OCH$_3$ | H | H | H |
| A12 | O(CH$_2$CH$_2$O)$_3$CH$_3$ | OCH$_2$CO-estradiol | OCH$_3$ | H | H | H |
| A13 | O(CH$_2$CH$_2$O)$_3$CH$_3$ | O(CH$_2$CH$_2$O)$_3$CH$_3$ | O(CH$_2$CH$_2$O)$_3$CH$_3$ | H | H | H |
| A14 | O(CH$_2$CH$_2$O)$_3$CH$_3$ | OCH$_2$CO-estradiol | O(CH$_2$CH$_2$O)$_3$CH$_3$ | H | H | H |
| A15 | O(CH$_2$CH$_2$O)$_3$CH$_3$ | O(CH$_2$CH$_2$O)$_{120}$CH$_3$ | OCH$_3$ | H | H | H |
| A16 | H | saccharide | OCH$_3$ | H | H | H |
| A17 | O(CH$_2$)$_3$OH | O(CH$_2$)$_3$OH | H | CH$_3$ | H | H |
| A18 | H | O(CH$_2$CH$_2$O)$_3$CH$_3$ | H | CH$_3$ | H | H |
| A19 | O(CH$_2$CH$_2$O)$_3$CH$_3$ | O(CH$_2$CH$_2$O)$_3$CH$_3$ | H | CH$_3$ | H | H |
| A20 | H | OCH$_2$CON-linker-oligo | H | CH$_3$ | H | H |
| A21 | H | OCH$_2$CO-estradiol | H | CH$_3$ | H | H |
| A22 | H | OCH$_2$CON(CH$_2$CH$_2$OH)$_2$ | H | CH$_3$ | H | H |
| A23 | O(CH$_2$CH$_2$O)$_3$CH$_3$ | O(CH$_2$CH$_2$O)$_{120}$CH$_3$ | H | CH$_3$ | H | H |
| A24 | O(CH$_2$CH$_2$O)$_3$CH$_3$ | OCH$_2$CON-linker-oligo | H | CH$_3$ | H | H |
| A25 | H | CH$_2$CON(CH$_3$)CH$_2$·(CHOH)$_4$CH$_2$OH | H | CH$_3$ | H | H |
| A26 | O(CH$_2$CH$_2$O)$_3$CH$_3$ | O(CH$_2$CH$_2$O)$_3$CH$_3$ | OH | CH$_3$ | H | H |
| A27 | O(CH$_2$CH$_2$O)$_3$CH$_3$ | O(CH$_2$CH$_2$O)$_3$CH$_3$ | F | CH$_3$ | H | H |
| A28 | O(CH$_2$CH$_2$O)$_3$CH$_3$ | O(CH$_2$CH$_2$O)$_3$CH$_3$ | H | CH$_2$(CH$_2$)$_6$OH | H | H |
| A29 | O(CH$_2$CH$_2$O)$_3$CH$_3$ | O(CH$_2$CH$_2$O)$_3$CH$_3$ | Br | H | H | H |
| A30 | O(CH$_2$CH$_2$O)$_3$CH$_3$ | O(CH$_2$CH$_2$O)$_3$CH$_3$ | NO$_2$ | H | H | H |
| A31 | O(CH$_2$CH$_2$O)$_3$CH$_3$ | O(CH$_2$CH$_2$O)$_3$CH$_3$ | COOH | H | H | H |
| A32 | O(CH$_2$CH$_2$O)$_3$CH$_3$ | O(CH$_2$CH$_2$O)$_3$CH$_3$ | CH$_2$ | H | H | H |
| A33 | O(CH$_2$CH$_2$O)$_3$CH$_3$ | O(CH$_2$CH$_2$O)$_3$CH$_3$ | H | C$_6$H$_5$ | H | H |
| A34 | O(CH$_2$CH$_2$O)$_3$CH$_3$ | O(CH$_2$CH$_2$O)$_3$CH$_3$ | H | CH$_2$CH$_3$ | H | H |
| A35 | O(CH$_2$CH$_2$O)$_3$CH$_3$ | O(CH$_2$CH$_2$O)$_3$CH$_3$ | H | CH$_3$ | H | H |
| A36 | O(CH$_2$CH$_2$O)$_3$CH$_3$ | O(CH$_2$CH$_2$O)$_3$CH$_3$ | H | CH$_3$ | H | H |
| A37 | OCH$_3$ | OCH$_3$ | H | CH$_3$ | H | H |
| A38 | H | OCH$_2$CO$_2$-glucosamine | H | CH$_2$(CH$_2$)$_6$OH | H | H |
| A39 | O(CH$_2$)$_3$OH | O(CH$_2$)$_3$OH | H | CH$_3$ or CH$_2$CH$_3$ | CH$_3$ or CH$_2$CH$_3$ | CH$_3$ or CH$_2$CH$_3$ |
| A40 | O(CH$_2$CH$_2$O)$_3$CH$_3$ | O(CH$_2$CH$_2$O)$_3$CH$_3$ | H | CH$_3$ or CH$_2$CH$_3$ | CH$_3$ or CH$_2$CH$_3$ | CH$_3$ or CH$_2$CH$_3$ |
| A41 | O(CH$_2$)$_3$OH | O(CH$_2$CH$_2$O)$_3$CH$_3$ | H | CH$_3$ or CH$_2$CH$_3$ | CH$_3$ or CH$_2$CH$_3$ | CH$_3$ or CH$_2$CH$_3$ |
| A42 | H | O(CH$_2$)$_n$CON-linker-oligo, n = 1,2,3 | H | CH$_3$ or CH$_2$CH$_3$ | CH$_3$ or CH$_2$CH$_3$ | CH$_3$ or CH$_2$CH$_3$ |
| A43 | H | O(CH$_2$)$_n$CO-estradiol, n = 1,2,3 | H | CH$_3$ or CH$_2$CH$_3$ | CH$_3$ or CH$_2$CH$_3$ | CH$_3$ or CH$_2$CH$_3$ |
| A44 | H | saccharide | H | CH$_3$ or CH$_2$CH$_3$ | CH$_3$ or CH$_2$CH$_3$ | CH$_3$ or CH$_2$CH$_3$ |
| A45 | O(CH$_2$)$_3$OH | O(CH$_2$)$_n$CON-linker-oligo, n = 1,2,3 | H | CH$_3$ or CH$_2$CH$_3$ | CH$_3$ or CH$_2$CH$_3$ | CH$_3$ or CH$_2$CH$_3$ |
| A46 | O(CH$_2$)$_3$OH | O(CH$_2$)$_n$CO-estradiol n = 1,2,3 | H | CH$_3$ or CH$_2$CH$_3$ | CH$_3$ or CH$_2$CH$_3$ | CH$_3$ or CH$_2$CH$_3$ |
| A47 | O(CH$_2$)$_3$OH | saccharide | H | CH$_3$ or CH$_2$CH$_3$ | CH$_3$ or CH$_2$CH$_3$ | CH$_3$ or CH$_2$CH$_3$ |
| A48 | O(CH$_2$CH$_2$O)$_3$CH$_3$ | O(CH$_2$)$_n$CON-liner-oligo, n = 1,2,3 | H | CH$_3$ or CH$_2$CH$_3$ | CH$_3$ or CH$_2$CH$_3$ | CH$_3$ or CH$_2$CH$_3$ |
| A49 | O(CH$_2$CH$_2$O)$_3$CH$_3$ | O(CH$_2$)$_n$CO-estradiol n = 1,2,3 | H | CH$_3$ or CH$_2$CH$_3$ | CH$_3$ or CH$_2$CH$_3$ | CH$_3$ or CH$_2$CH$_3$ |
| A50 | O(CH$_2$CH$_2$O)$_3$CH$_3$ | saccharide | H | CH$_3$ or CH$_2$CH$_3$ | CH$_3$ or CH$_2$CH$_3$ | CH$_3$ or CH$_2$CH$_3$ |
| A51 | O(CH$_2$CH$_2$O)$_3$CH$_3$ | O(CH$_2$)$_n$CON-liner-oligo, n = 1,2,3 | H | H | CH$_3$ or CH$_2$CH$_3$ | CH$_3$ or CH$_2$CH$_3$ |
| A52 | O(CH$_2$CH$_2$O)$_3$CH$_3$ | O(CH$_2$CH$_2$O)$_3$CH$_3$ n = 1,2,3 | H | H | CH$_3$ or CH$_2$CH$_3$ | CH$_3$ or CH$_2$CH$_3$ |
| A53 | O(CH$_2$CH$_2$O)$_3$CH$_3$ | O(CH$_2$CH$_2$O)$_3$CH$_3$ | H | H | CH$_2$(CH$_2$)$_2$OH | CH$_2$(CH$_2$)$_2$OH |
| A54 | O(CH$_2$CH$_2$O)$_3$CH$_3$ | O(CH$_2$)$_n$CON-linker-oligo n = 1,2,3 | H | H | CH$_2$(CH$_2$)$_2$OH | CH$_2$(CH$_2$)$_2$OH |
| A55 | O(CH$_2$CH$_2$O)$_3$CH$_3$ | O(CH$_2$)$_n$CON-linker-oligo n = 1,2,3 | H | CH$_3$ or CH$_2$CH$_3$ | CH$_2$(CH$_2$)$_2$OH | CH$_2$(CH$_2$)$_2$OH |

TABLE B-continued

Representative Substituents for Texaphyrin Macrocycles A1–A50 of the Present Invention.
Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A56 | $O(CH_2CH_2O)_3CH_3$ | $O(CH_2CH_2O)_3CH_3$ | H | $CH_3$ or $CH_2CH_3$ | $CH_2(CH_2)_2OH$ | $CH_2(CH_2)_2OH$ |

A substituent on the $R_5$, $R_{10}$, $R_{11}$ or $R_{12}$ position of the macrocycle may be derivatized after condensation of the macrocycle. Substituents may include an alkyl group having up to 5 carbon atoms or a phenyl group which may be further derivatized with a nitro, carboxyl, sulfonic acid, hydroxyl, halide or alkoxy where the alkyl of the alkoxy may be hydroxyalkyl and like, as described in U.S. Pat. No. 5,252,720 and application Ser. No. 08/135,118.

EXAMPLE 8

Further Derivatives of Texaphyrin

One skilled in the art of organic synthesis in light of the present disclosure could extend and refine the basic synthetic chemistry outlined in this application, in U.S. Pat. No. 5,252,720 and in application Ser. No. 08/135,118 so as to produce texaphyrins having various substituents, yet having basic utility to those specifically detailed in the present examples. For example, polyether-linked polyhydroxylated groups, catechol (i.e. benzene diol) derivatives bearing further hydroxyalkyl substituents off the tripyrrane-derived portion of the macrocycle, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride or p-nitrophenol acetate would generate activated acyl species suitable for attachment to monoclonal antibodies or other biomolecules of interest. Standard in situ coupling methods (e.g. 1,1'-carbonyldiimidazole (CDI)) could be used to effect the conjugation.

The selectivity of the texaphyrins may be enhanced by covalently linking oligonucleotides onto the periphery of the macrocycle. Amides, ethers and thioethers are representative of linkages which may be used for this purpose. Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligodeoxynucleotide-texaphyrin complex conjugates may be designed so as to provide optimal catalytic interaction between a target nucleic acid and the bound texaphyrin. The oligonucleotide may be large enough to bind probably at least 15 nucleotides of complementary nucleic acid.

A general method for preparing oligonucleotides of various lengths and sequences is described by Caracciolo et al. (1989). Preferred oligonucleotides resistant to in vivo hydrolysis may contain a phosphorothioate substitution at each base (*J. Org. Chem.*, 55:4693–4699, 1990). Oligodeoxynucleotides or their phosphorothioate analogues may be synthesized using an Applied Biosystem 380B DNA synthesizer (Applied Biosystems, Inc., Foster City, Calif.). Specific methods for preparing texaphyrin-oligonucleotide conjugates are disclosed in PCT publication WO 94/29316, the disclosure of which is incorporated herein by reference.

Another means of gaining selectivity may be to covalently link the texaphyrin complex to a sapphyrin (sap) molecule, (U.S. Pat. Nos. 5,159,065; 5,120,411; 5,041,078, all incorporated by reference herein.) Since sapphyrins bind DNA, K ~$10^6$ M$^{-1}$, (U.S. Ser. No. 07/964,607, incorporated by reference herein) the linked texaphyrin-sapphyrin complex (txph-sap) could effectively increase the texaphyrin concentration at locations adjacent to the sapphyrin binding sites. Sapphyrins have a higher fluorescent quantum yield than texaphyrins, allowing greater fluorescence detection. A laser system may be employed where the molecules are optimized to the laser wavelength; an excited sapphyrin may transfer its energy to the conjugated texaphyrin for detection. The texaphyrin molecule may further be designed to pass through cell membranes for selective radiosensitization.

New texaphyrin derivatives are characterized fully using normal spectroscopic and analytical means, including, X-ray diffraction methods.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A method of magnetic resonance image enhancement in a subject, the method comprising:

administering to the subject an effective amount of a texaphyrin; and imaging the subject using a magnetic resonance device;

wherein the texaphyrin has structure:

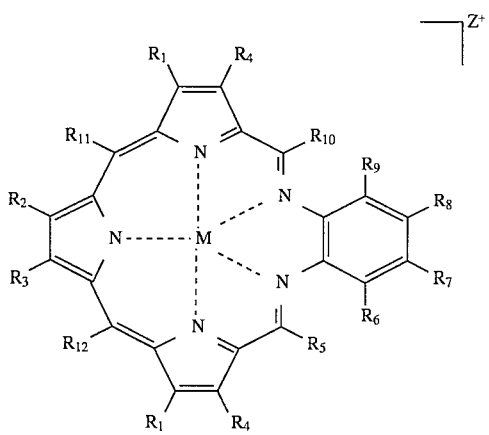

wherein

M is a paramagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, a catalytic group, or a couple to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group;

at least one of $R_5$, $R_6$, $R_9$, $R_{10}$, $R_{11}$ and $R_{12}$ is other than hydrogen; and Z is an integer less than or equal to 5.

2. The method of claim 1 where the paramagnetic metal cation is selected from the group consisting of Mn(II), Mn(III), Fe(III) and all trivalent lanthanide metals other than La(III), Lu(III) and Pm(III).

3. The method of claim 1 where M is Gd(III).

4. The method of claim 1 where the couple is an amide, disulfide, thioether or ether covalent bond.

5. The method of claim 1 where the catalytic group is selected from the group consisting of imidazole, guanidine, substituted saccharides, amino acids, derivatives of amino acids, polymers of amino acids, and texaphyrin metal complexes.

6. The method of claim 1 where the site-directing molecule has binding specificity for localization to a treatment site.

7. The method of claim 1 where the site-directing molecule is selected from the group consisting of an oligonucleotide, an antibody, a hormone, a hormone mimic, a peptide having affinity for a biological receptor, and a sapphyrin molecule.

8. The method of claim 1 where at least one of $R_5$ and $R_{10}$–$R_{12}$ is other than hydrogen; and when $R_5$ is other than hydrogen, then $R_6$ is hydrogen, halide other than iodide, or hydroxyl; and when $R_{10}$ is other than hydrogen, then $R_9$ is hydrogen, halide other than iodide, or hydroxyl.

9. The method of claim 1 where at least one of $R_6$ and $R_9$ is other than hydrogen; and when $R_6$ is other than hydrogen, then $R_5$ is hydrogen or methyl; and when $R_9$ is other than hydrogen, then $R_{10}$ is hydrogen or methyl.

10. The method of claim 1 where $R_5$ and $R_{10}$ are aryl having an $R_{13}$ substituent where $R_{13}$ is hydrogen, nitro, carboxy, sulfonic acid, hydroxy, oxyalkyl or halide.

11. The method of claim 1 where each of $R_1$–$R_{12}$ is any one of the substituents for $R_1$–$R_{12}$ set out in Tables A and B.

12. The method of claim 1 where $R_1$ is $CH_2(CH_2)_2OH$, $R_2$ and $R_3$ are $CH_2CH_3$, $R_4$, $R_5$ and $R_{10}$ are $CH_3$, $R_6$ and $R_9$ are H, and $R_7$ and $R_8$ are $O(CH_2CH_2O)_3CH_3$ or $R_7$ is H or $OCH_3$ and $R_8$ is a site-directing molecule or a couple to a site-directing molecule.

13. The method of claim 12 where $R_{11}$ and $R_{12}$ are H or $CH_3$.

14. The method of claim 1 where the texaphyrin is selected from texaphyrins A1–A56 of Tables A and B.

15. A method of detection of neoplastic tissue in a subject, the method comprising:

administering to the subject a texaphyrin in an amount effective to enhance a magnetic resonance image of neoplastic tissue; and detecting neoplastic tissue by magnetic resonance imaging of the subject;

wherein the texaphyrin has structure:

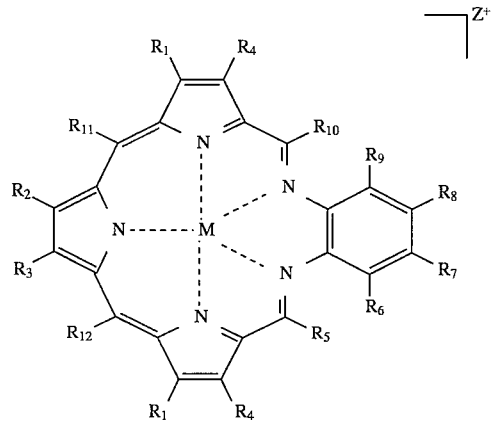

wherein

M is a paramagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, a catalytic group, or a couple to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group;

at least one of $R_5$, $R_6$, $R_9$, $R_{10}$, $R_{11}$ and $R_{12}$ is other than hydrogen; and Z is an integer less than or equal to 5.

16. The method of claim 15 where the neoplastic tissue is a tumor.

* * * * *